(12) United States Patent
Ryu et al.

(10) Patent No.: US 12,097,059 B2
(45) Date of Patent: Sep. 24, 2024

(54) TELESCOPIC COLUMN FOR X-RAY IMAGING APPARATUS

(71) Applicant: DRGEM CORPORATION, Gyeonggi-do (KR)

(72) Inventors: Hoon Ryu, Gyeonggi-do (KR); Wonsup Yoon, Gyeonggi-do (KR)

(73) Assignee: DRGEM CORPORATION, Gyeonggi-Do (KR)

( * ) Notice: Subject to any disclaimer, the term of this patent is extended or adjusted under 35 U.S.C. 154(b) by 0 days.

(21) Appl. No.: 18/574,537

(22) PCT Filed: Jan. 6, 2023

(86) PCT No.: PCT/KR2023/000337
§ 371 (c)(1),
(2) Date: Dec. 27, 2023

(87) PCT Pub. No.: WO2023/132706
PCT Pub. Date: Jul. 13, 2023

(65) Prior Publication Data
US 2024/0180505 A1    Jun. 6, 2024

(30) Foreign Application Priority Data

Jan. 7, 2022   (KR) .................. 10-2022-0002461
Mar. 23, 2022  (KR) .................. 10-2022-0035791

(51) Int. Cl.
*A61B 6/00* (2024.01)
*B25J 18/02* (2006.01)

(52) U.S. Cl.
CPC ............ *A61B 6/447* (2013.01); *A61B 6/4405* (2013.01); *B25J 18/025* (2013.01)

(58) Field of Classification Search
CPC ........................... A61B 6/4405; B25J 18/025
See application file for complete search history.

(56) References Cited

U.S. PATENT DOCUMENTS

2007/0211863 A1*  9/2007  Graumann .......... A61B 6/4405
                                                   378/197
2016/0199013 A1*  7/2016  Moreno Vallejo ... A61B 6/4452
                                                   378/194

FOREIGN PATENT DOCUMENTS

| JP | 2000-023958 A | 1/2000 |
| JP | 2004-033415 A | 2/2004 |
| JP | 2008-237324 A | 10/2008 |
| KR | 10-2011-0062397 A | 6/2011 |
| KR | 10-2012-0095460 A | 8/2012 |

(Continued)

OTHER PUBLICATIONS

International Search Report for PCT/KR2023/000337 mailed on Apr. 14, 2023.

*Primary Examiner* — Dani Fox
(74) *Attorney, Agent, or Firm* — The PL Law Group, PLLC

(57) ABSTRACT

A telescopic column for an X-ray imaging apparatus includes a main column, a sub-column liftably arranged on one side of the main column, and a weight compensator arranged on an opposite side of the main column to compensate for a weight of the sub-column, wherein the weight compensator includes a cam formed such that a radius of winding of a wire therearoud changes according to a lifting height of the sub-column, and an elastic member configured to extend and contract according to rotation of the cam to provide elastic force to compensate for the weight of the sub-column.

10 Claims, 26 Drawing Sheets

(56) References Cited

FOREIGN PATENT DOCUMENTS

KR  10-2018-0066839 A   6/2018
KR  10-2469173 B1   11/2022

* cited by examiner

TELESCOPIC COLUMN FOR X-RAY IMAGING APPARATUS

CROSS REFERENCE TO RELATED APPLICATIONS AND CLAIM OF PRIORITY

This application claims benefit under 35 U.S.C. 119, 120, 121, or 365(c), and is a National Stage entry from International Application No. PCT/KR2023/000337, filed Jan. 6, 2023, which claims priority to the benefit of Korean Patent Application Nos. 10-2022-0002461 filed on Jan. 7, 2022 and 10-2022-0035791 filed on Mar. 23, 2022, in the Korean Intellectual Property Office, the entire contents of which are incorporated herein by reference.

BACKGROUND

1. Technical Field

The present disclosure relates to a telescopic column for an X-ray imaging apparatus that can be easily elevated with uniform force.

2. Background Art

In recent years, when X-ray imaging is required for critically ill patients with limited mobility or during surgery, it is often necessary to move a mobile X-ray imaging apparatus to the required location without requiring the patient to enter the X-ray room.

Examples of a mobile X-ray imaging apparatus are disclosed in Korean Patent Application Publication Nos. 10-2011-0062397 and 10-2012-0095460.

FIG. 1 is a diagram of a conventional mobile X-ray imaging apparatus. The mobile X-ray imaging apparatus includes a body 1 equipped with a display 27, a column 2 mounted vertically on the body 1, an arm 3 mounted on the column and an X-ray source 4 provided on the arm 3. The column 2 may include a main column 5 and a sub-column 6, and the arm 3 may be provided with a plurality of unit arms 7, 8, and 9 that are telescopically extendable. The length of the column 2 and arm 3 may be shortened for safety during transportation. Then, the column 2 and arm 3 may be extended during imaging to position the X-ray source 4 at an appropriate point.

The conventional mobile X-ray imaging apparatus has a separate drive source for extending or shortening the length (height) of the column 2, but it is difficult to move the column 2 quickly enough to position the X-ray source 4 at a point desired by the user within a short time.

In another example, a weight is used to compensate for the weight of the arm 3 and the sub-column 6 such that the column 2 can be manually extended or shortened, and the sub-column 6 can be elevated together with the arm 3 even with a small amount of force. However, when the weight is compensated for by a weight or the like, the overall weight of the mobile X-ray imaging apparatus may be increased, thereby reducing its mobility.

SUMMARY

It is an object of the present disclosure to provide a telescopic column for an X-ray imaging apparatus that can be quickly and easily positioned at a desired point manually without the need for a separate driving source or weight.

It is another object of the present disclosure to provide a telescopic column for an X-ray imaging apparatus that can compensate for the weight of the arm and sub-column using the elastic force of an elastic member.

It is another object of the present disclosure to provide a telescopic column for an X-ray imaging apparatus that can raise an arm and a sub-column with uniform force, regardless of changes in the elastic force of the elastic member according to the height at which the arm and the sub-column are lifted.

In accordance with one aspect of the present disclosure, provided is a telescopic column for an X-ray imaging apparatus, the telescopic column including a main column, a sub-column liftably arranged on one side of the main column, and a weight compensator arranged on an opposite side of the main column to compensate for a weight of the sub-column, wherein the weight compensator includes a cam formed such that a radius of winding of a wire therearoud changes according to a lifting height of the sub-column, and an elastic member configured to extend and contract according to rotation of the cam to provide elastic force to compensate for the weight of the sub-column.

According to one embodiment, the weight compensator may include a first fixed pulley arranged on the main column, a movable pulley arranged to be lifted and lowered with respect to the first fixed pulley, a first wire having one end coupled to the main column and an opposite end coupled to the sub-column via the movable pulley and the first fixed pulley, a cam unit arranged to rotate in connection with the lifting and lowering of the movable pulley, and the elastic member arranged to extend and contract in connection with the rotation of the cam unit to provide elastic force to the sub-column.

According to another embodiment, the weight compensator may include a second wire having one end coupled to one side of the movable pulley and an opposite end wound on one side of the cam unit, and a third wire having one end coupled to the elastic member and an opposite end wound on an opposite side of the cam unit.

According to another embodiment, the cam unit may include a cam formed such that a radius of winding of the second wire therearoud changes when the cam rotates, and a cam pulley arranged on one side of the cam to rotate integrally with the cam, the third wire being wound around the cam pulley.

According to another embodiment, a torque of the cam caused by lifting and lowering of the movable pulley may act as a reaction torque against a torque of the cam pulley caused by extension and contraction of the elastic member.

According to another embodiment, the sub-column may include a first sub-column liftably arranged on one side of the main column, and a second sub-column liftably arranged on one side of the first sub-column.

According to another embodiment, the telescopic column may further include an interlocking mechanism configured to lift and lower the second sub-column in connection with lifting and lowering of the first sub-column, wherein the interlocking mechanism may include a second fixing pulley arranged at an upper end of the first sub-column, a fourth wire having one end coupled to the main column and an opposite end coupled to the second sub-column via the second fixing pulley.

According to another embodiment, the weight compensator further may include a third fixed pulley arranged on one side of the elastic member, wherein the second wire may be wound on one side of the cam unit via the third fixed pulley.

According to another embodiment, the sub-column may include a first sub-column liftably arranged on one side of the main column, and a second sub-column liftably arranged on one side of the first sub-column. The telescopic column may further include an interlocking mechanism configured to lift and lower the second sub-column in connection with lifting and lowering of the first sub-column, wherein the interlocking mechanism may include a fourth fixing pulley arranged at an upper end of the first sub-column, and a fourth wire having one end coupled to the one side of the main column and an opposite end coupled to one side of the second sub-column via the fourth fixing pulley.

According to the telescopic column for X-ray imaging apparatus according to the present disclosure, the column may be quickly and easily extended or shortened manually without a separate drive source or weight by using the elastic force of an elastic member to compensate for the weight of the arm and sub-column.

DETAILED DESCRIPTION

Figure 1:
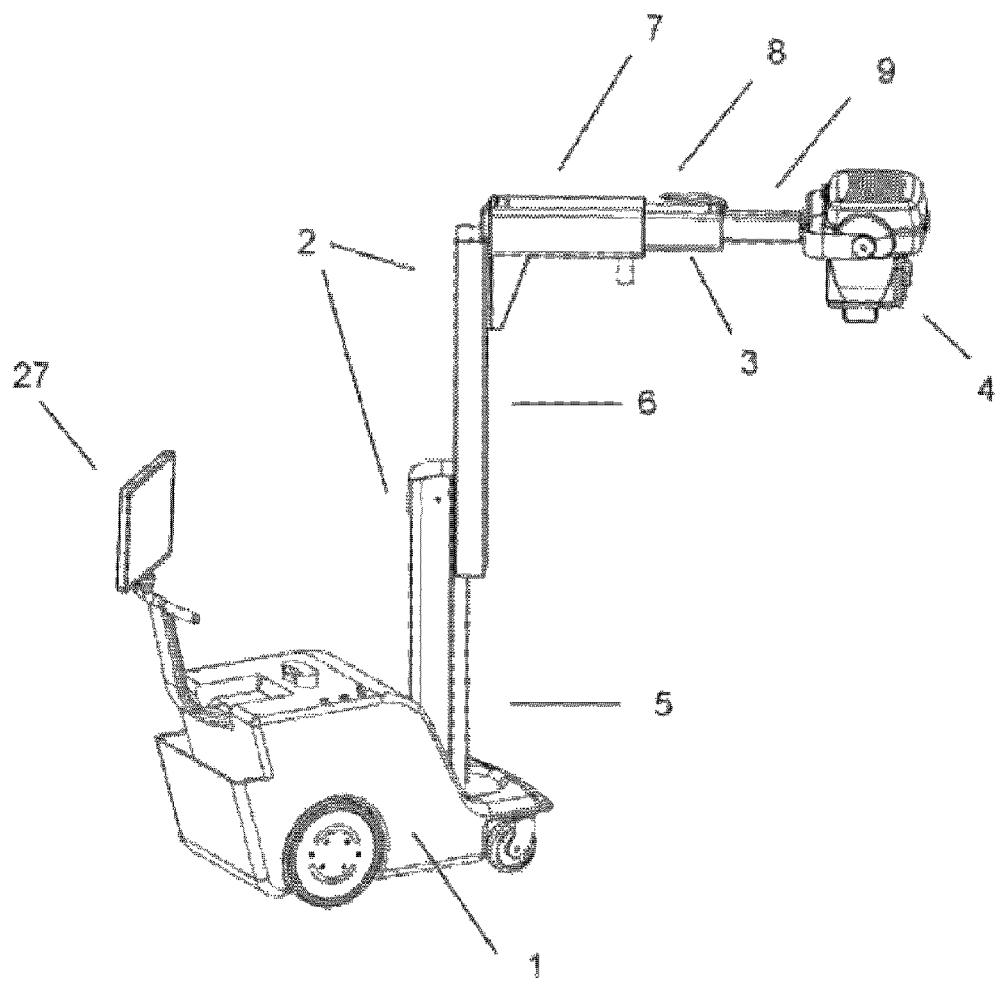
FIG. 1 is a configuration diagram of a conventional mobile X-ray imaging apparatus.

Hereinafter, embodiments of the present disclosure will be described in detail with reference to the accompanying drawings. However, the embodiments described below are intended only to describe the disclosure in detail so that those having ordinary skill in the art to which the disclosure pertains can easily practice the invention, and are not intended to limit the scope of the disclosure. Throughout the description of various embodiments of the present disclosure, the same reference numerals are used to refer to components having the same technical features.

A telescopic column for an X-ray imaging apparatus according to the present disclosure includes a main column, a sub-column liftably mounted on the main column, and a weight compensator configured to compensate for the weight of the sub-column such that a user can easily elevate the sub-column with little effort. Further, the weight compensator includes a cam unit having a cam and a cam pulley to elevate the sub-column with uniform force regardless of changes in the lifting height of the sub-column. Embodiments of the present disclosure will now be described in detail with reference to the accompanying drawings.

FIGS. 2 to 14 illustrate a telescopic column for an X-ray imaging apparatus according to a first embodiment of the present disclosure.

Figure 2:
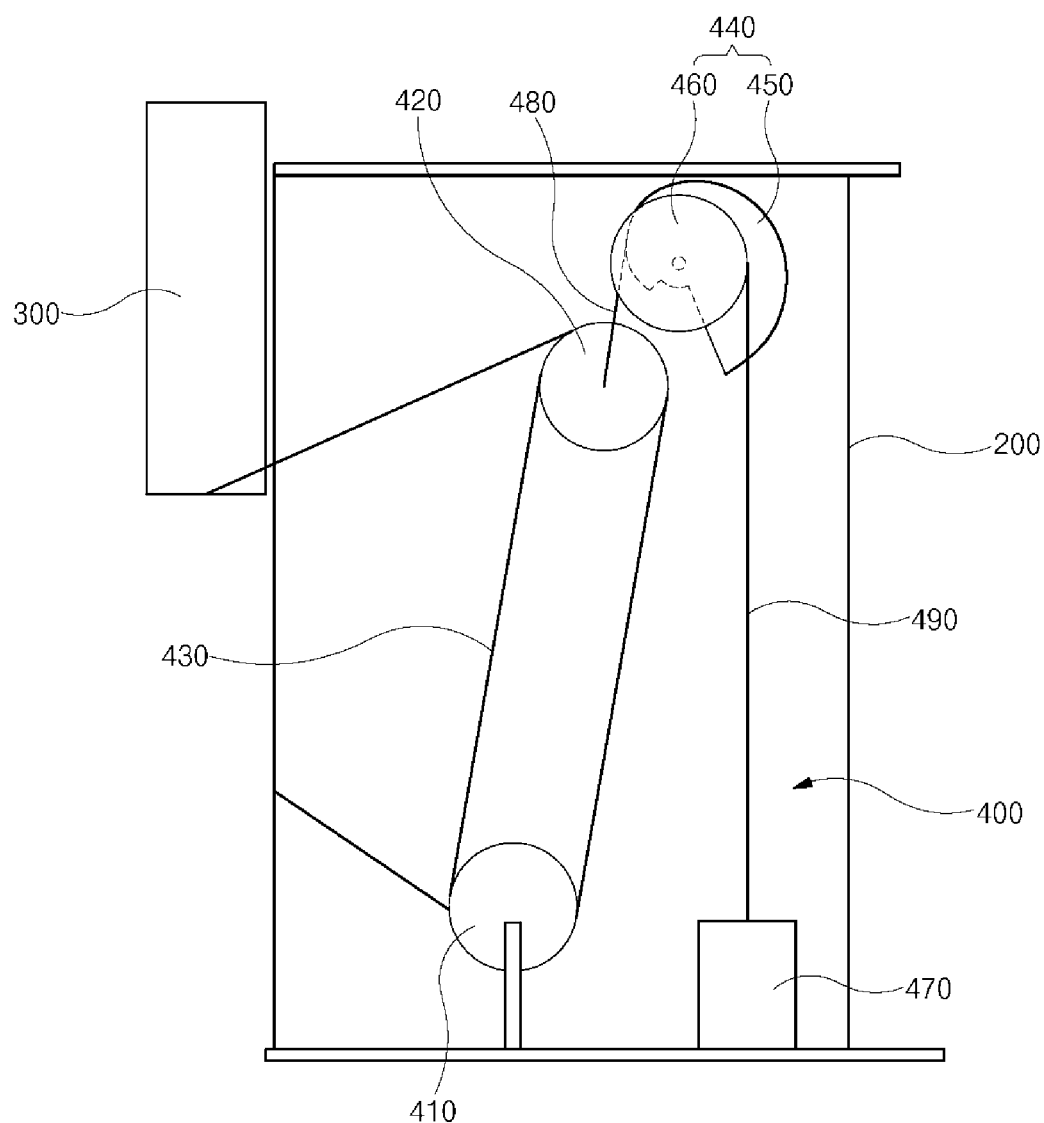
FIGS. 2 and 3 are configuration diagrams of a telescopic column for an X-ray imaging apparatus according to a first embodiment of the present disclosure.
Figure 3:
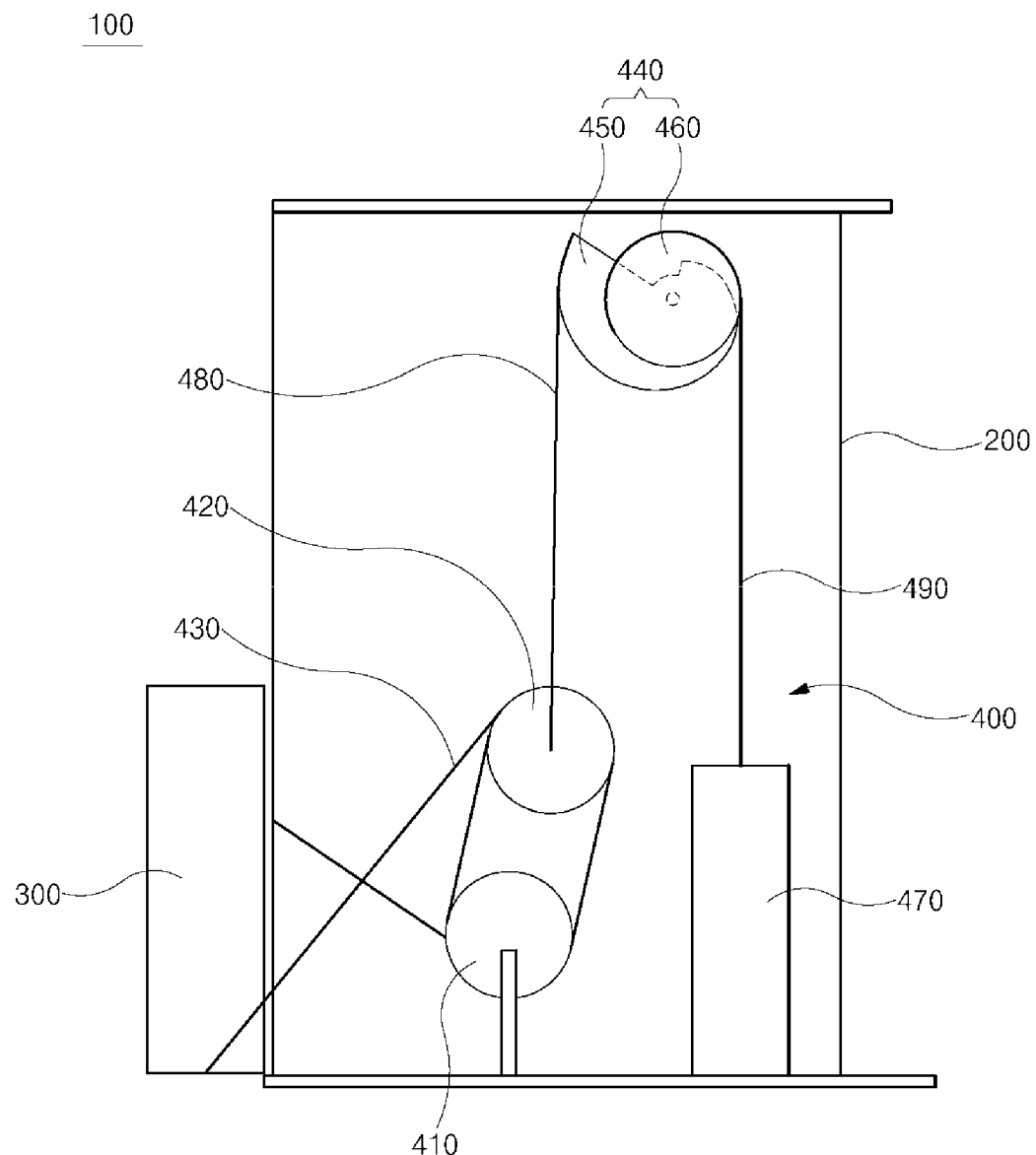

As shown in FIGS. 2 and 3, a telescopic column 100 for an X-ray imaging apparatus includes a main column 200, a sub-column 300 liftably mounted on the main column 200, and a weight compensator 400 configured to compensate for the weight of the sub-column 300.

The weight compensator 400 includes a first fixed pulley 410 and a movable pulley 420, which are mounted on the main column 200, and a first wire 430 connecting the main column 200 and the sub-column 300, a cam 450 that varies the winding radius of a second wire 480 connected to the movable pulley 420 based on the lifting height of the sub-column 300, and an elastic member 470 arranged to extend and contract with the rotation of the cam 450 to provide elastic force to the sub-column 300 via a third wire 490.

According to the first embodiment of the present disclosure, as the weight of the sub-column 300 is compensated for by the weight compensator 400, a user may easily lift and lower the sub-column 300 at a constant speed with little effort. Furthermore, in lifting and lowering the sub-column 300, the weight compensator 400 allows the sub-column 300 to be lifted and lowered at a constant speed by applying a uniform force regardless of the height of the sub-column 300.

The main column 200 may be installed vertically on the body 1 (see FIG. 1) of the mobile X-ray imaging apparatus, and a hollow part is formed therein to allow the weight compensator 400 including multiple pulleys and wires to be installed. In this case, the main column 200 may be axially rotatably installed on the body 1 of the mobile X-ray imaging apparatus.

The sub-column 300 is liftably disposed on one side of the main column 200. In one example, a slide rail (not shown) may be formed on one side of the main column 200, and the sub-column 300 may be provided with multiple rollers (not shown) slidably movable along the slide rail of the main column 200 in a vertical direction.

An arm 3 (see FIG. 1) having an X-ray source 4 (see FIG. 1) at an end thereof may be liftably mounted on one side of the sub-column 300. In this case, the arm may be multi-stage telescopically formed, and the weight compensator 400 compensates for the weight of the sub-column 300 including the X-ray source 4 and the arm 3.

The weight compensator 400 may include the first fixed pulley 410 rotatably disposed at a lower end of the main column 200, the movable pulley 420 liftably disposed above and spaced apart from the first fixed pulley 410, and the first wire 430 extending through the first fixed pulley 410 and the movable pulley 420 to connect the main column 200 and the sub-column 300.

Here, the number of first fixed pulleys 410 and movable pulleys 420 may be appropriately selected as needed. In one example, a pair of movable pulleys 420 may be arranged side by side above one first fixed pulley 410. The first wire 430 may be coupled to one side of the main column 200 at one end, wound around the circumference of the movable pulleys 420 and the first fixed pulley 410, and coupled to the sub-column 300 at an opposite end.

As the first wire 430 connects the main column 200 and the sub-column 300 via the first fixed pulley 410 and the movable pulley 420, the movable pulley 420 is lifted and lowered with respect to the first fixed pulley 410 when the sub-column 300 is lifted and lowered with respect to the main column 200.

In this case, the lifting and lowering of the sub-column 300 may be performed manually by the user, and the weight compensator 400 serves to make it possible to easily raise the sub-column 300 at a constant speed with little effort, despite the weight of the sub-column 300.

To this end, the elastic member 470, which provides elastic force to the sub-column 300, is disposed in the hollow part of the main column 200. The elastic member 470 is arranged to extend and retract in connection with the lifting and lowering of the movable pulley 420, and provides an elastic force to the sub-column 300 in connection with the movable pulley 420 to compensate for the weight of the sub-column 300. For example, when the elastic force provided by the elastic member 470 is in balance with the weight of the sub-column 300, the user may easily lift and lower the sub-column 300 at a constant speed with little effort.

While the figures show an extensible tension spring as an example of the elastic member 470, this is merely one embodiment, and various types of the elastic member 470 that provide elastic force, such as a gas spring or a torsion spring, may be applied as needed.

The elastic force provided by the elastic member 470 may change as the sub-column 300 is lifted and lowered. For example, when a tension spring is employed as the elastic member 470, the tension spring may be increasingly stretched as the sub-column 300 is lowered, thereby increasing the elastic force and thereby increasing the force required for the user to lower the sub-column.

According to the first embodiment of the present disclosure, the cam unit 440 is provided to enable the sub-column 300 to be lifted and lowered with uniform force regardless of changes in the lifting height of the sub-column 300.

The cam unit 440 may be arranged to rotate in connection with the lifting and lowering of the traveling pulley 420. For example, one end of the second wire 480 may be coupled to one side of the movable pulley 420 and the opposite end thereof may be wound on one side of the cam unit 440.

Additionally, the elastic member 470 may be arranged to extend and contract in connection with the rotation of the cam unit 440. For example, one end of the third wire 490 may be coupled to the elastic member 470 and the opposite end thereof may be coupled to the opposite side of the cam unit 440.

More specifically, the cam unit 440 may include a cam 450 formed such that a winding radius of the second wire 480 changes when rotated, and a cam pulley 460 arranged on one side of the cam 450 to rotate integrally with the cam 450, the third wire 490 being wound around the cam pulley 460. As an example, a pair of cam pulleys 460 may be arranged on both sides of the cam 450, and a pair of third wires 490 extending side by side from the upper end of the elastic member 470 may each be wound on the pair of cam pulleys 460.

In this case, when the sub-column 300 rises, the tension spring contracts and the cam pulley 460 rotates such that the third wire 490 is unwound. At this time, as the cam 450 rotates together with the cam pulley 460, the second wire 480 is wound around the cam 450, and the second wire 480 pulls the movable pulley 420 upward. Thus, the movable pulley 420 moves upward with respect to the first fixed pulley 410.

Conversely, when the sub-column 300 is lowered, the movable pulley 420 moves down together with the sub-column 300, and the cam 450 rotates such that the second wire 480 is unwound. At this time, as the cam pulley 460 rotates together with the cam 450, the third wire 490 is wound around the cam pulley 460, and the tension spring is extended by the third wire 490.

Here, the cam 450 has a cam profile that is formed such that the winding radius of the second wire 480 changes when the cam is rotated. This is intended to cause the torque of the cam pulley 460 due to the extension and contraction of the elastic member 470 and the torque of the cam 450 due to the lifting and lowering of the movable pulley 420 to act as a reaction torque against each other, such that the sub-column 300 can be lifted and lowered with uniform force regardless of its height.

Figure 4:
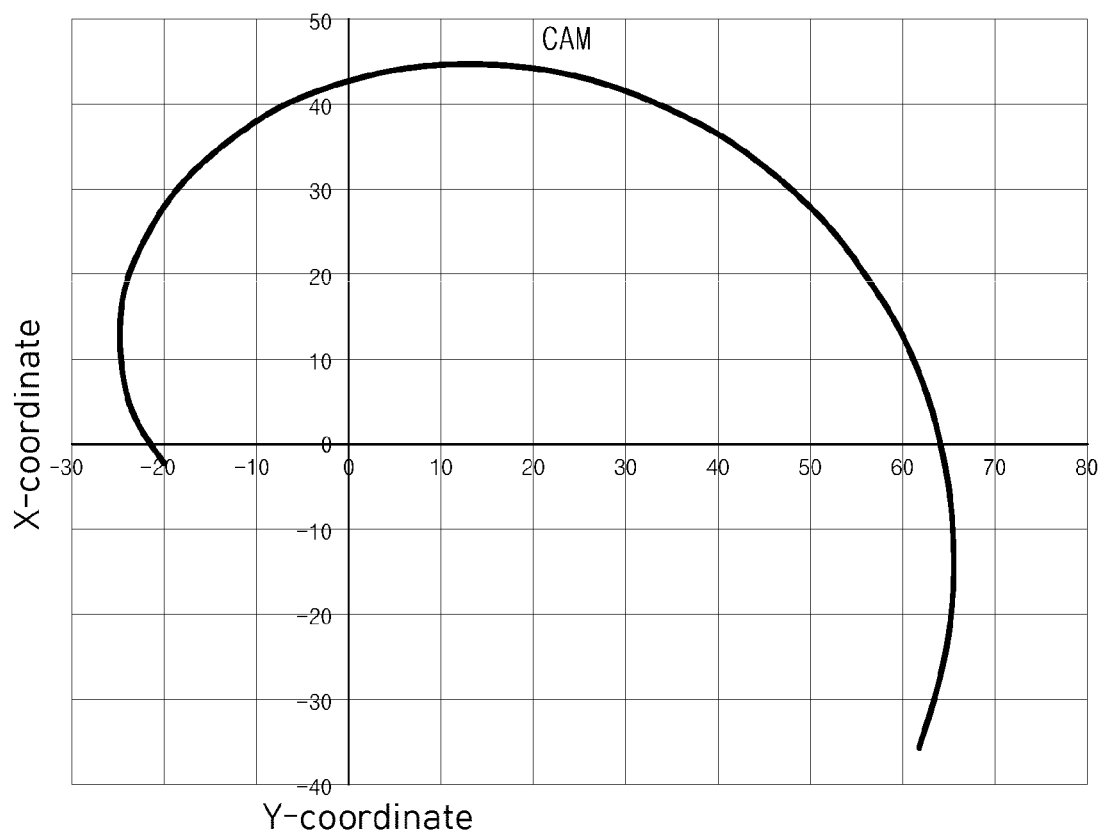
FIG. 4 depicts a cam profile calculated according to the first embodiment of the present disclosure.

FIG. 4 is a graph depicting a cam profile according to the first embodiment of the present disclosure. The cam profile according to the rotation angle of the cam pulley 460 is obtained by calculating the spring force of the tension spring and the torque of the cam pulley 460 according to the rotation angle of the cam pulley 460 and calculating the radius of the cam 450 from the torque of the cam 450 for compensating for the torque.

Figure 5:
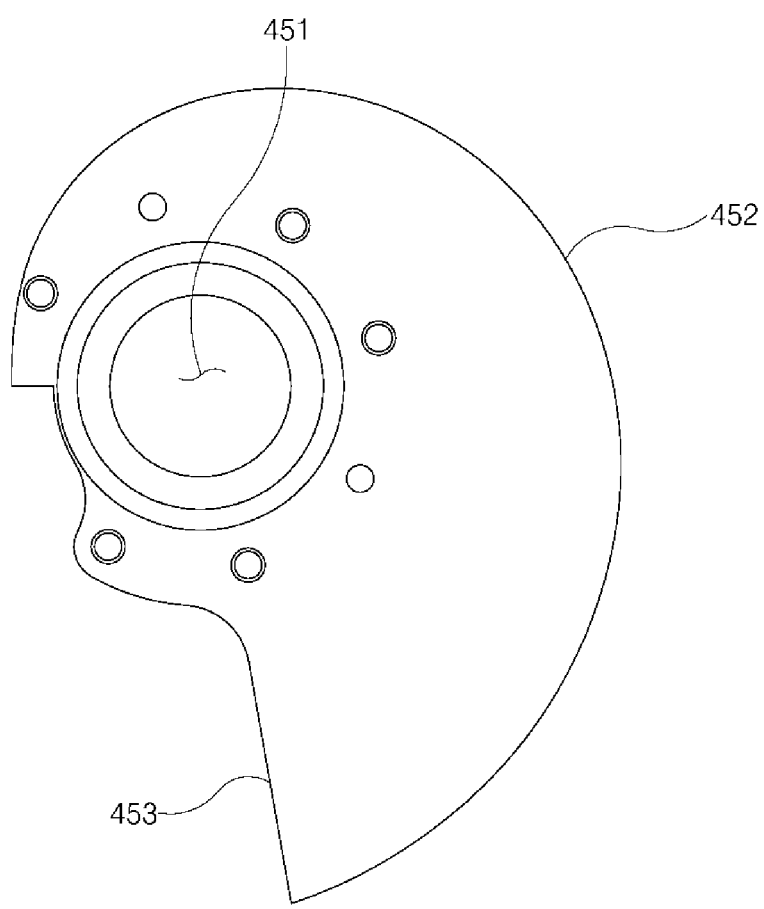
FIG. 5 is a side view of a cam according to the first embodiment of the present disclosure.
Figure 6:
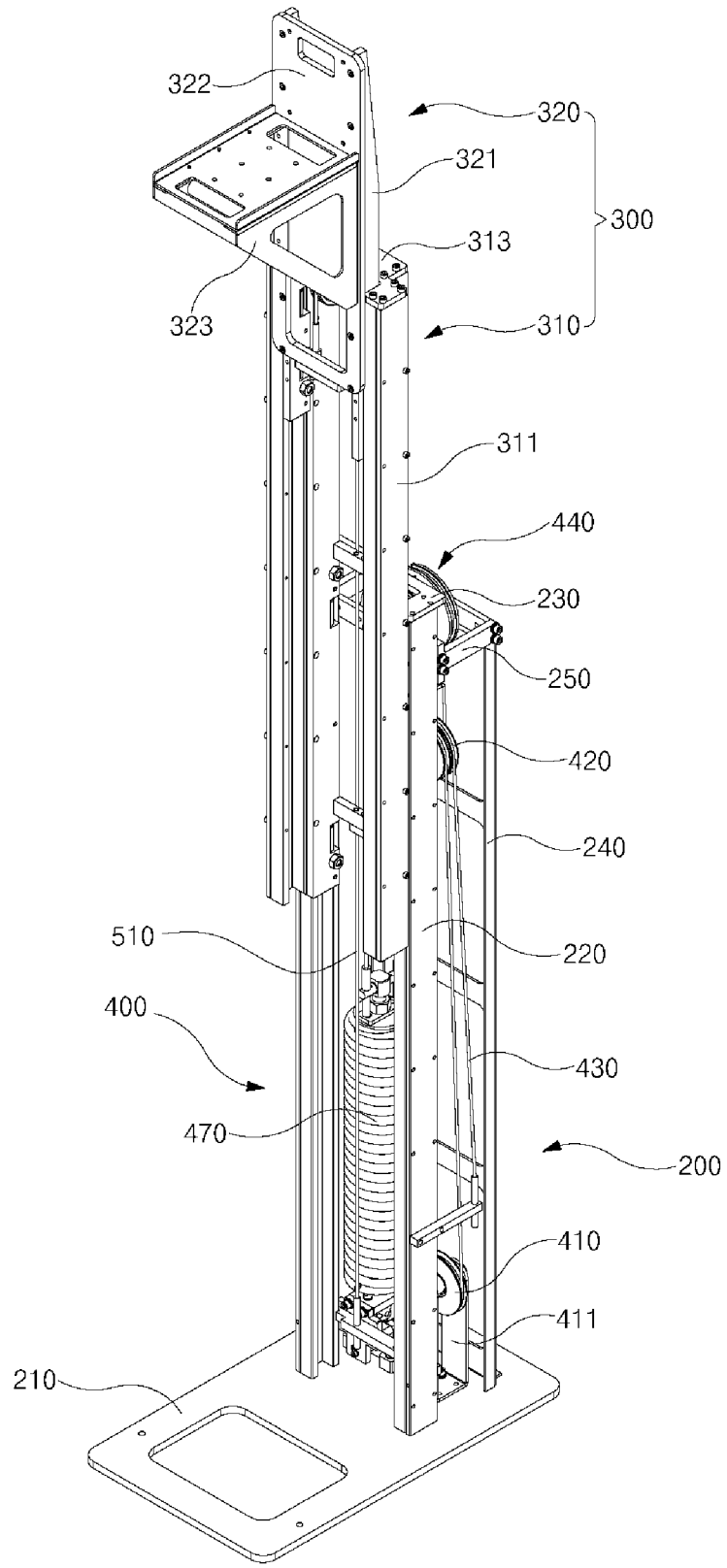
FIGS. 6 and 7 are perspective views of the telescopic column according to the first embodiment of the present disclosure.

Referring to FIG. 5, the cam 450 has a shaft hole 451 on one side for inserting a rotation shaft, and has a radius gradually increasing in one direction along the circumference in a predetermined angle range. In addition, it has a curved surface 452 formed in a spiral shape within a predetermined angle range corresponding to the lifting range of the sub-column 300 as a whole, and a straight surface 453 extending from one end of the spiral curved surface 452 toward the rotation shaft. In addition, a second wire fixing part 454 (not shown in FIG. 5 but shown in FIG. 14) to which the opposite end of the second wire 480 is fixed is formed on one side of the straight surface 453, and a first winding groove 456 (not shown in FIG. 5 but shown in FIG. 14) for winding the second wire 480 is formed on the spiral curved surface 452 of the cam 450.

Accordingly, when the tension spring is extended and the torque of the cam pulley 460 increases as the sub-column 300 is lowered, the winding radius of the second wire 480 of the cam 450 gradually increases to increase the torque of the cam 450. On the other hand, when the sub-column 300 is lifted, the tension spring contracts. Thus, the torque of the cam pulley 460 is reduced, and the winding radius of the second wire 480 of the cam 450 gradually decreases, thereby reducing the torque of the cam 450.

In this operation, the torque of the cam 450 acts as a reaction torque with respect to the torque of the cam pulley 460 to compensate for the difference between the elastic force of the tension spring and the weight of the sub-column 300, and the user may be allowed to lift the sub-column 300 with uniform force regardless of the height of the sub-column 300 or the extension length of the tension spring.

Referring to FIGS. 6 to 10, it can be seen in more detail that the telescopic column 100 for an X-ray apparatus includes the main column 200, the sub-column 300 liftably mounted on one side of the main column 200, and the weight compensator 400 mounted on the main column 200 to compensate for the weight of the sub-column 300.

A support plate 210 may be coupled to the lower end of the main column 200 to support the main column 200. This support plate 210 may be coupled to the body 1 of the mobile X-ray imaging apparatus. While the support plate 210 is shown as having a rectangular shape in the figures, this is merely an example. A circular support plate 210 may be rotatably coupled to the body 1 of the mobile X-ray imaging apparatus.

The main column 200 includes a pair of main frames 220 arranged vertically and spaced apart from each other by a predetermined distance in the width direction of the support plate 210, and an upper end frame 230 coupled to an upper end of the pair of main frames 220, a support frame 240 arranged in parallel with the main frames 220 at a predetermined distance from the rear of the main frames 220, and a connection frame 250 that connects the upper end of the support frame 240 to the rear end of the main frames 220. As an example, the connection frame 250 may be formed by joining four unit frames into a rectangular shape.

The main frames 220 serve to guide the lifting direction of the sub-column 300. The multiple pulleys, cam unit 440, and elastic member 470, which constitute the weight compensator 400, are arranged in the space between the main frames 220 and the support frame 240.

The sub-column 300 may include a first sub-column 310 liftably mounted on one side of the main column 200, and a second sub-column 320 liftably mounted on one side of the first sub-column 310.

The first sub-column 310 is liftably mounted to the front of the main column 200, and includes a pair of sub-frames 311 vertically slidably coupled to the front of the pair of main frames 220, and a pair of movable frames 312 mounted alongside the sub-frames 311 on the inner side of the rear of the pair of sub-frames 311. The pair of sub-frames 311 and the pair of movable frames 312 are integrally coupled by a cover frame 313 coupled to the top and bottom thereof.

The second sub-column 320 is liftably mounted to the front of the first sub-column 310. The second sub-column 320 includes a pair of lifting frames 321 each vertically slidably coupled to an inner side of the pair of sub-frames 311, a lifting plate 322 coupled to a front of the pair of lifting frames 321 and disposed in front of the sub-frames 311, and an arm support bracket 323 coupled to a front of the lifting plate 322. Although not shown in the figures, the arm support bracket 323 may be coupled to the arm 3 that is multi-stage telescopic and includes the X-ray source 4 at an end thereof.

Hereinafter, the lifting structure of the first sub-column 310 and the second sub-column 320 with respect to the main column 200 will be described in detail with reference to FIGS. 11 and 12.

Figure 11:
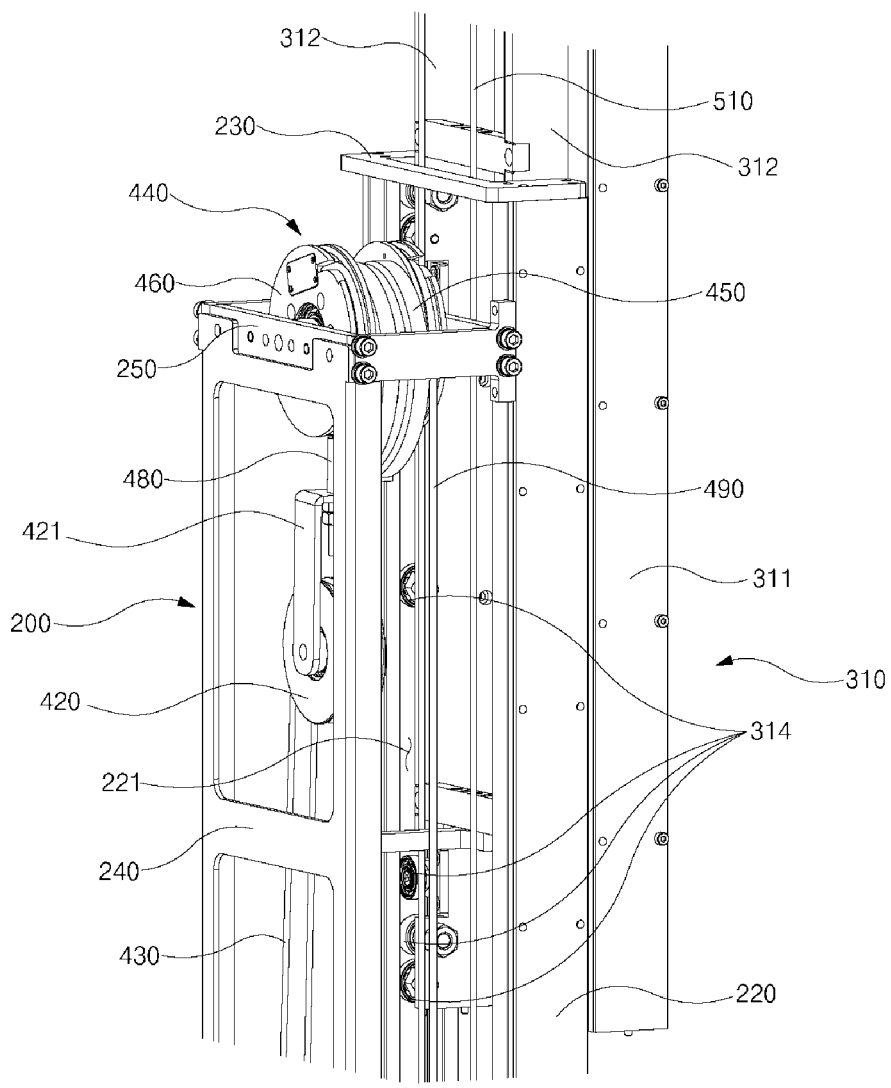
FIG. 11 is a partially enlarged view illustrating the slide engagement of a main column and a first sub-column according to the first embodiment of the present disclosure.

As shown in FIG. 11, the first sub-column 310 is provided with multiple first rollers 314 on the outside of the pair of movable frames 312. The first rollers 314 are slidably coupled to a first slide groove 221 formed inside the main frames 220 of the main column 200. Accordingly, when the first sub-column 310 is lifted or lowered with respect to the main column 200, the first rollers 314 of the movable frames 312 move along the first slide groove 221 of the main frames 220.

Figure 12:
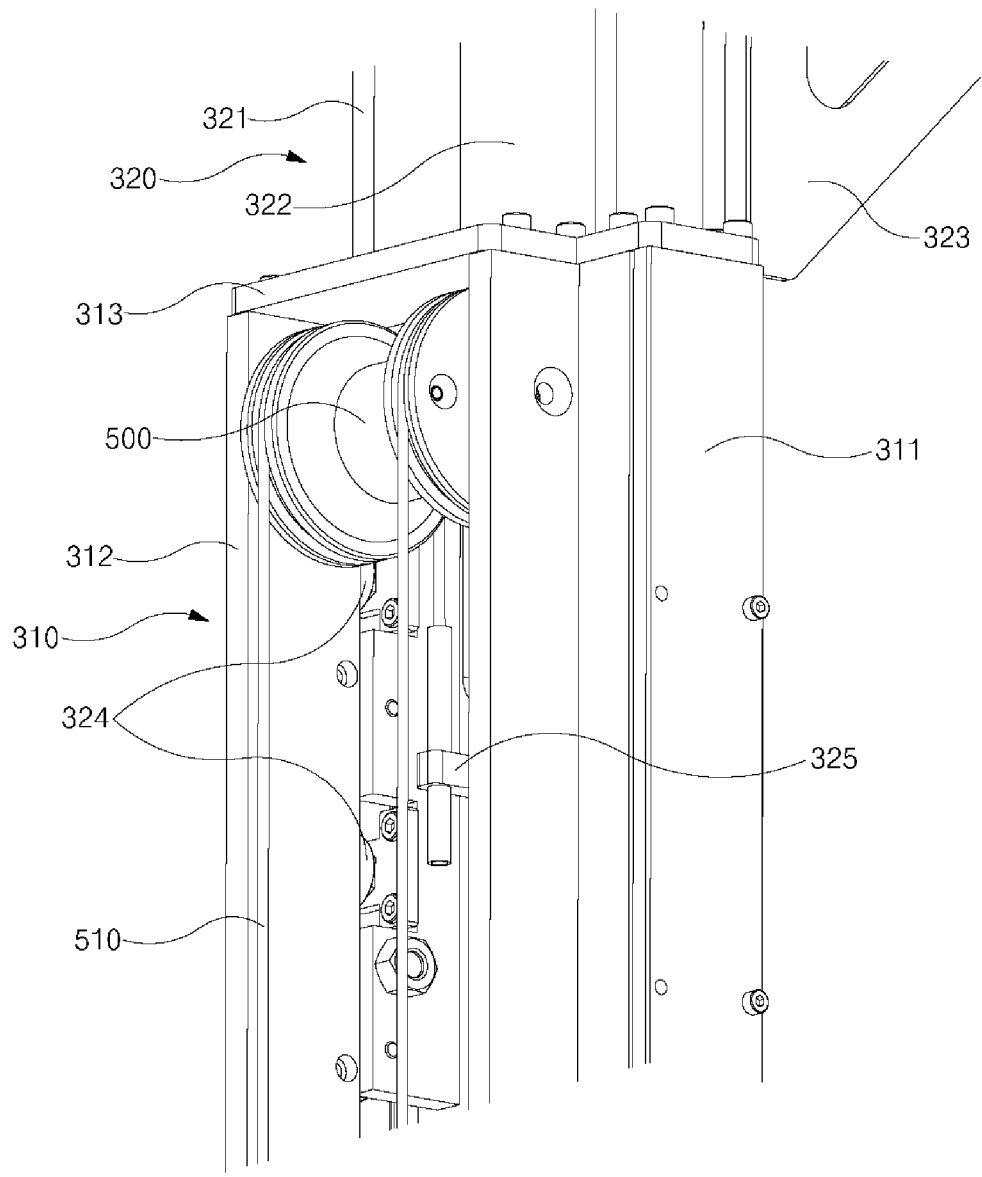
FIG. 12 is a partially enlarged view illustrating the slide engagement of the first sub-column and a second sub-column according to the first embodiment of the present disclosure.

As shown in FIG. 12, the second sub-column 320 is provided with multiple second rollers 324 on the outside of the pair of lifting frames 321. The second rollers 324 are slidably coupled to a second slide groove (not shown) formed inside the sub-frame 311 of the sub-column 310. Accordingly, when the second sub-column 320 is lifted and lowered with respect to the first sub-column 310, the second rollers 324 of the lifting frame 321 move along the second slide groove of the sub-frame 311.

Figure 13:
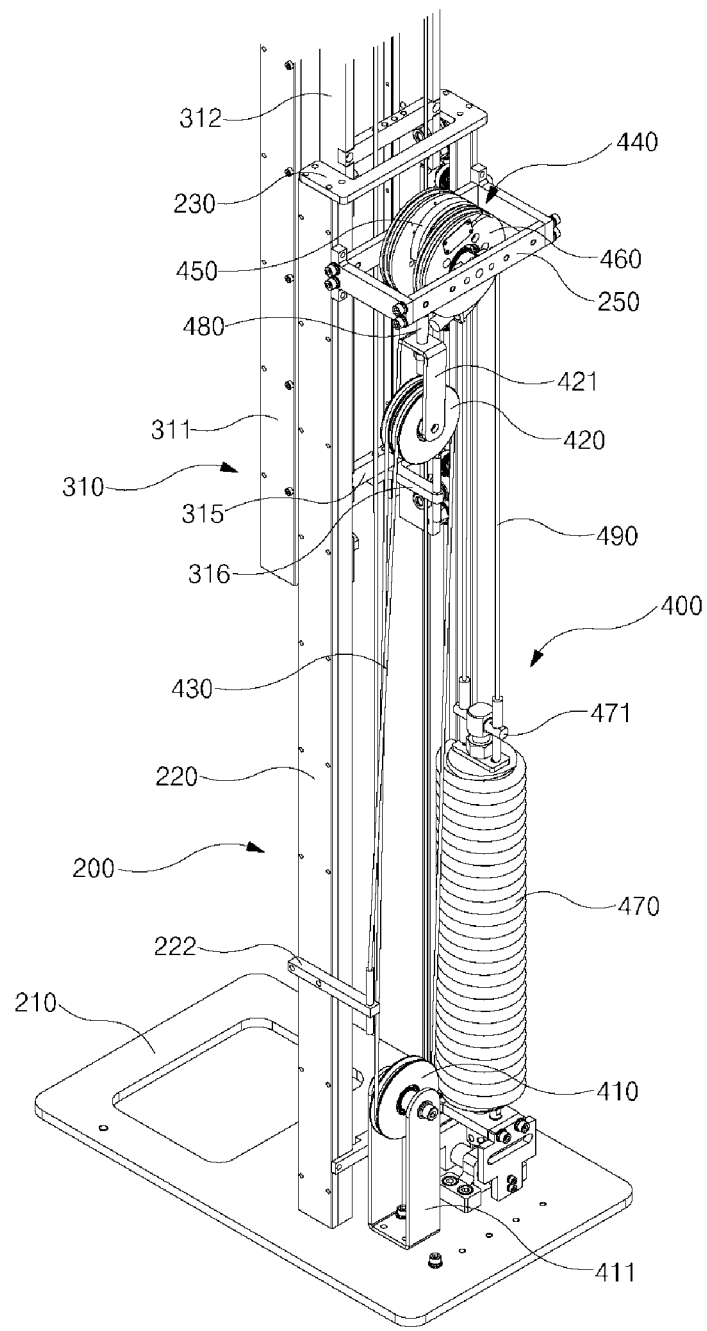
FIG. 13 is a partially enlarged view of the main column showing a weight compensator according to the first embodiment of the present disclosure.

FIG. 13 is a partially enlarged view of the main column showing the weight compensator. For simplicity, the support frame is omitted. As shown in the figure, the first fixed pulley 410 is arranged at the lower end of the main column 200. The first fixed pulley 410 may be rotatably supported by a support bracket 411 coupled to the top of the support plate 210.

Additionally, the cam unit 440 is rotatably mounted on the connection frame 250 at the upper end of the support frame 240. The cam unit 440 may be rotatably supported by, for example, a rotation shaft that extends through the connection frame 250 in the front-back direction.

Figure 14:
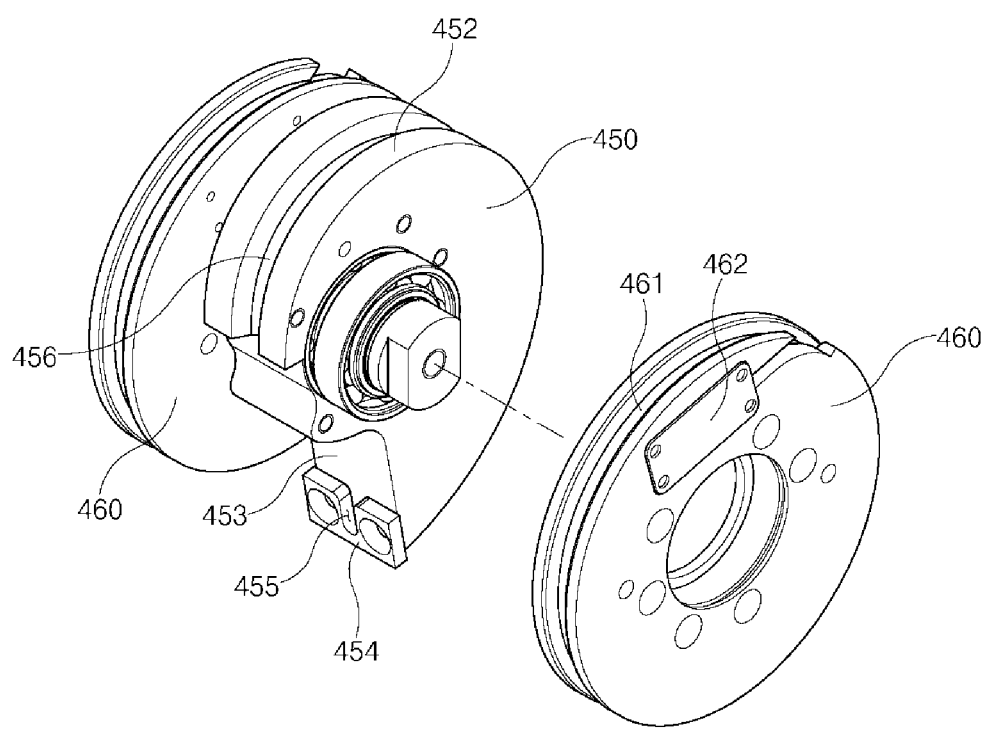
FIG. 14 is an exploded perspective view of a cam unit according to the first embodiment of the present disclosure.
Figure 15:
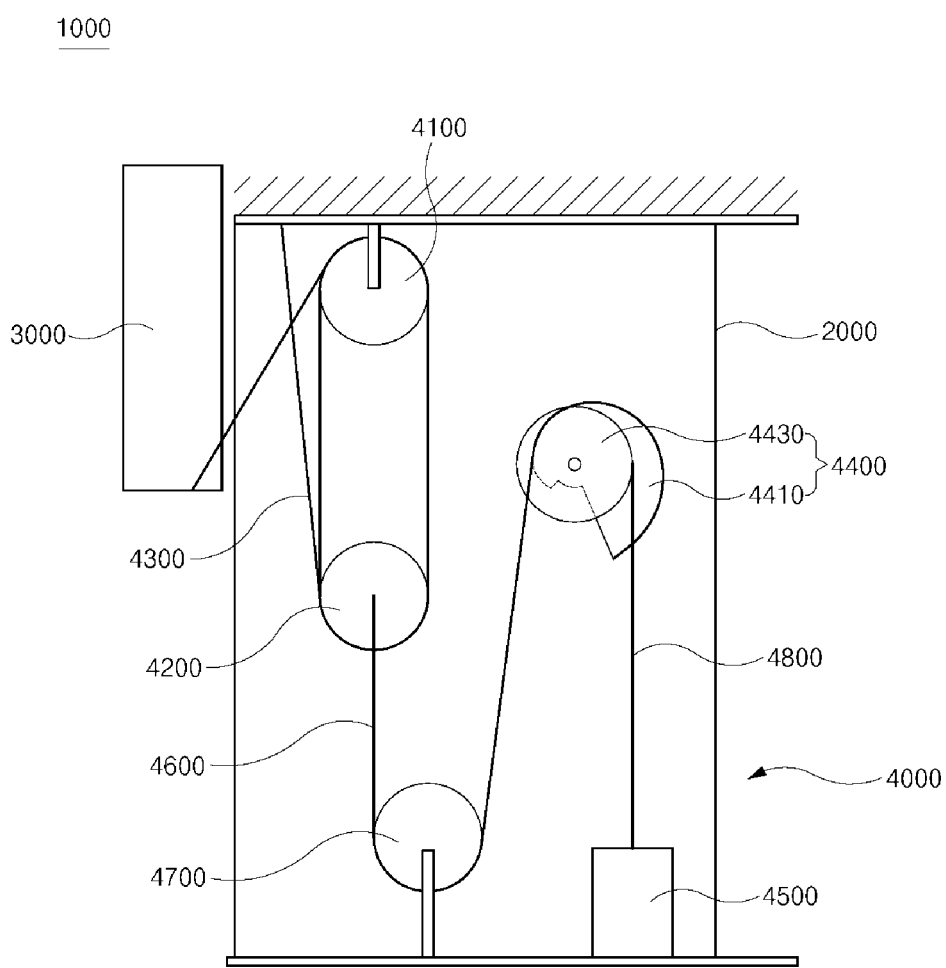
FIGS. 15 and 16 are configuration diagrams of a telescopic column for an X-ray imaging apparatus according to a second embodiment of the present disclosure.
Figure 16:
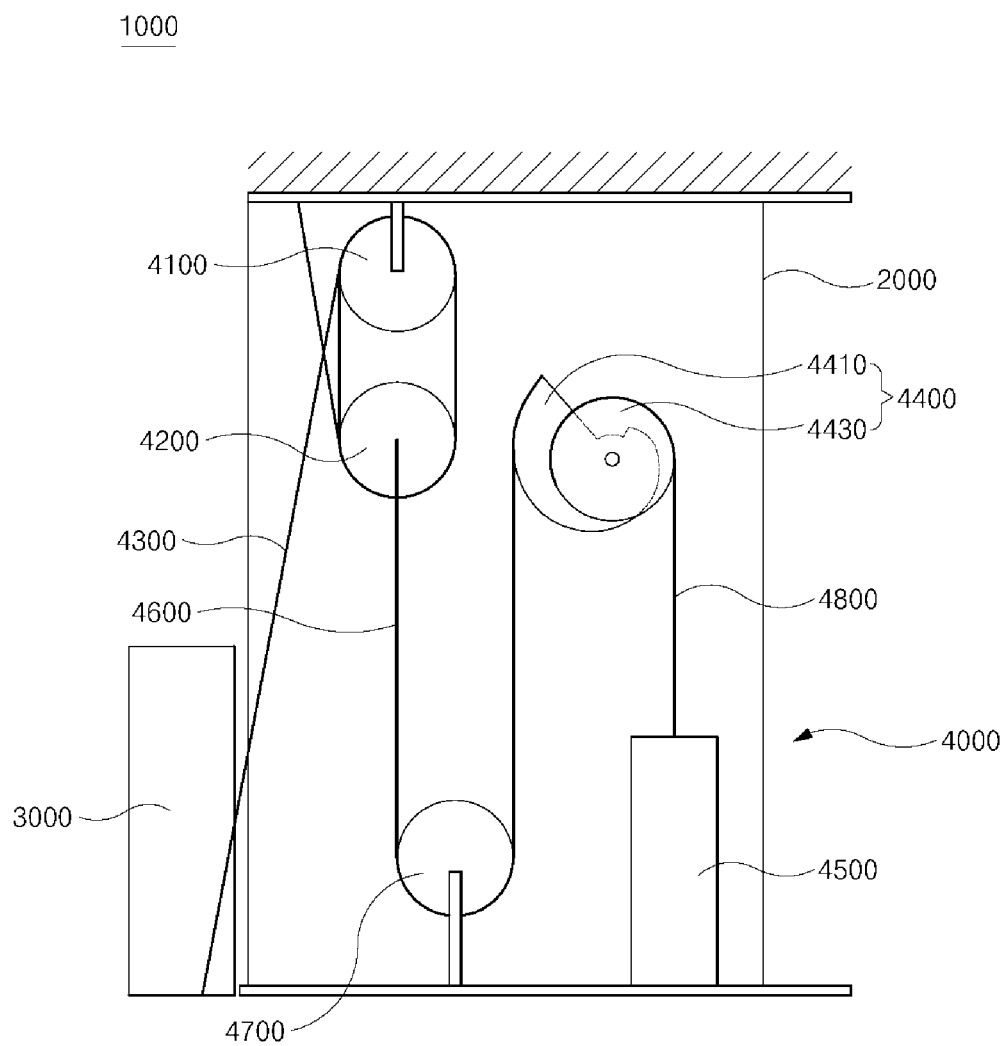
Figure 17:
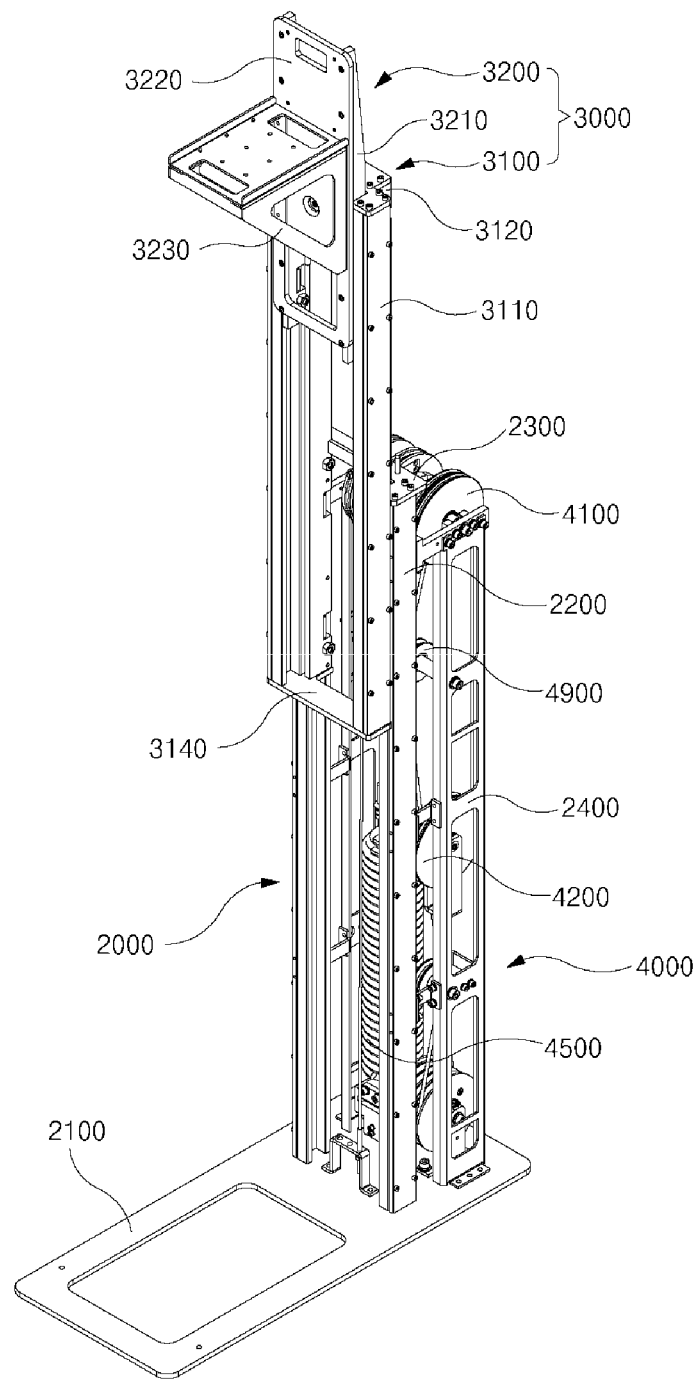
FIGS. 17 and 18 are perspective views of the telescopic column according to the second embodiment of the present disclosure.
Figure 18:
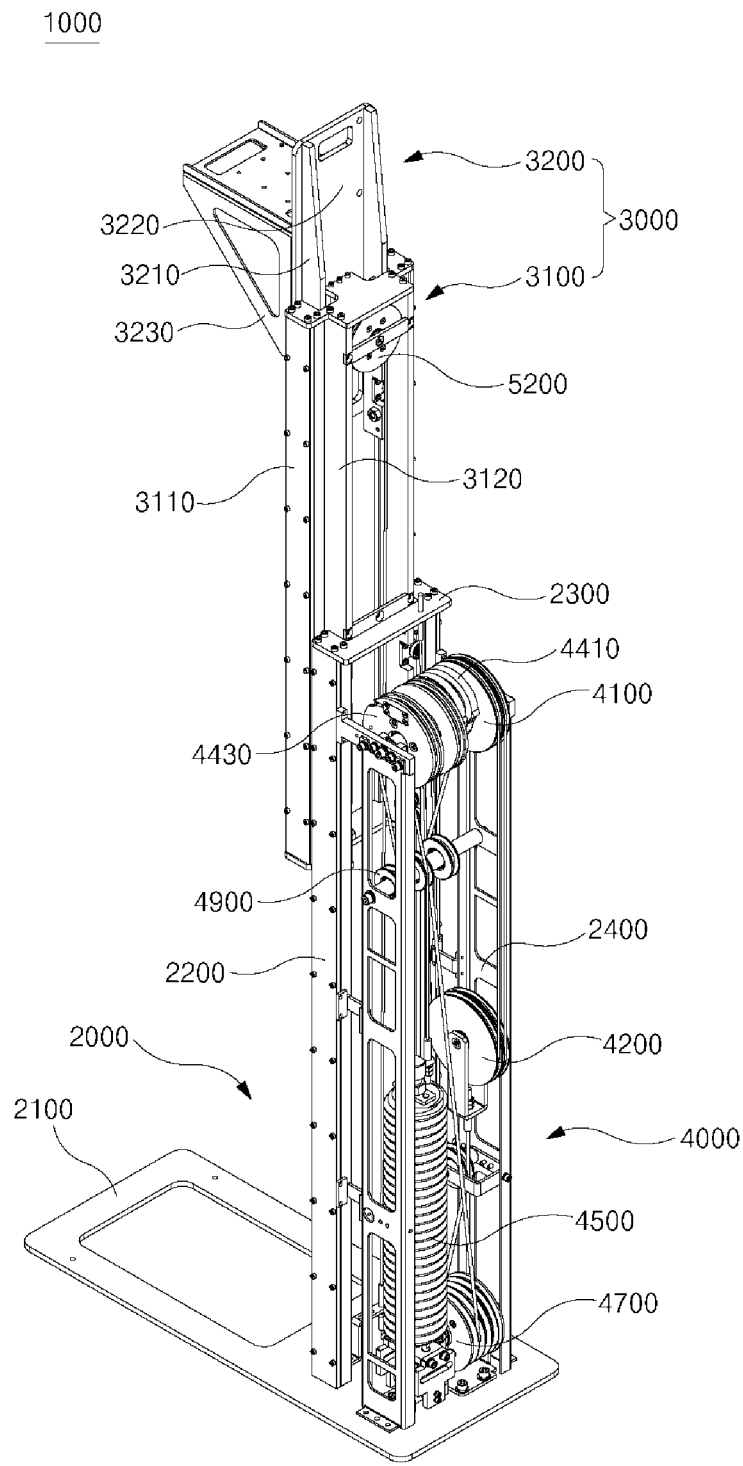
Figure 19:
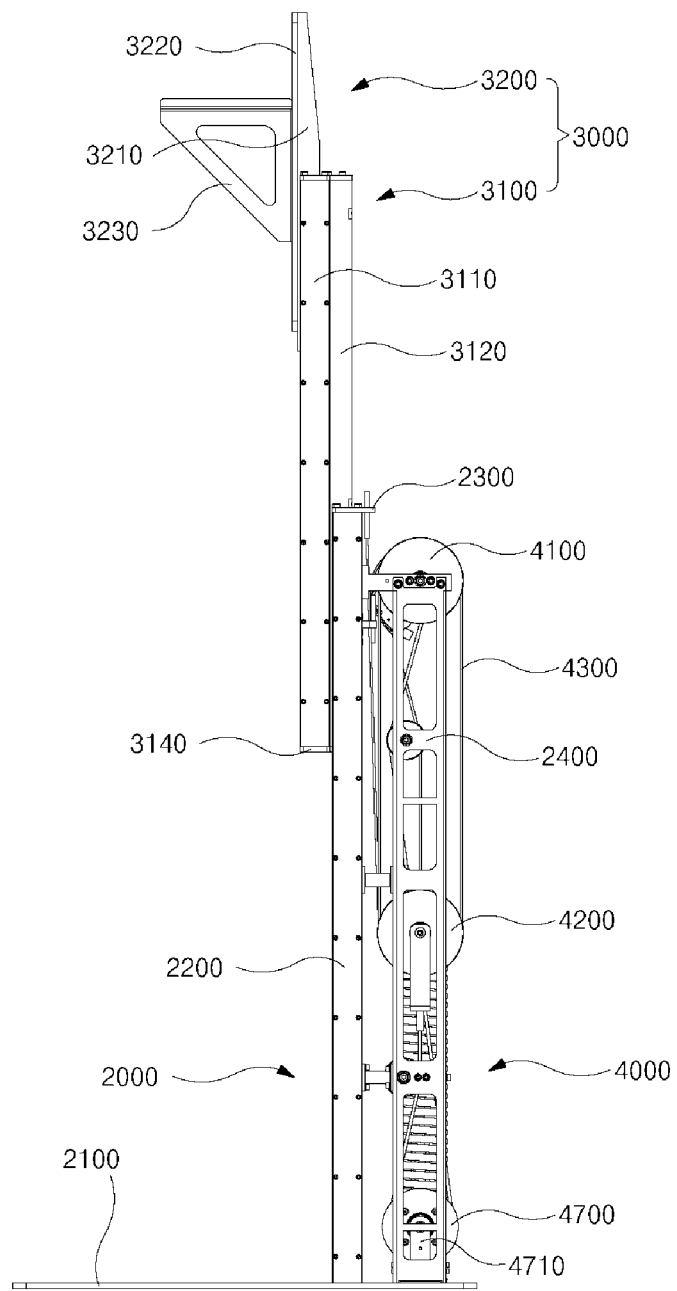
FIG. 19 is a side view of the telescopic column according to the second embodiment of the present disclosure.

As shown in FIG. 14, the cam unit 440 includes a cam 450 whose winding radius changes, and at least one cam pulley 460 arranged on one side of the cam 450 to integrally rotate with the cam 450. The figure shows an example in which a pair of cam pulleys 460 is coupled, one on each side of the cam 450. The cam 450 and the cam pulleys 460 may be formed as one body. In another example, the cam 450 and the cam pulley 460 may be formed as separate members and then rotatably coupled to each other to form one body.

As described with reference to FIG. 5, the cam 450 has the curved surface 452 formed in a spiral shape within a predetermined angle range corresponding to the lifting range of the sub-column 300, and the straight surface 453 extending from one end of the spiral curved surface 452 toward the rotation shaft. In addition, the second wire fixing part 454 having a groove 455 is formed on one side of the straight surface 453 to fix the opposite end of the second wire 480, and the first winding groove 456 for winding the second wire 480 is formed on the spiral curved surface 452 of the cam 450.

Additionally, a second winding groove 461 is formed along the outer circumferential surface of the cam pulley 460, and a third wire fixing part 462 is formed on one side of the cam pulley 460. One end of the third wire 490 is coupled to the third wire fixing part 462. Accordingly, when the cam pulley 460 rotates, the third wire 490 is wound around the second winding groove 461 of the cam pulley 460

Referring to FIG. 13, a pair of movable pulleys 420 is liftably and rotatably arranged below the cam unit 440. For example, the rotation shaft of the pair of movable pulleys 420 may be coupled to the lower end of the lifting bracket 421, which has an inverted U shape.

In this case, one end of the second wire 480 is coupled to the upper end of the lifting bracket 421, and the opposite end of the second wire 480 is connected to the second wire fixing part 454 through the first winding groove 456 of the cam 450. Accordingly, when the movable pulley 420 is lifted or lowered, the second wire 480 is wound around or unwound from the cam 450.

The first fixed pulley 410 is arranged below the movable pulley 420. As an example, the first fixed pulley 410 may be rotatably supported at the upper end of the U-shaped support bracket 411, which is coupled to the top surface of the support plate 210.

A first wire 430 is connected between the first fixed pulley 410 and a pair of movable pulleys 420. One end of the first wire 430 is coupled to one side of the main column 200, and the opposite end thereof coupled to one side of the first sub-column 310 via the pair of movable pulleys 420 and the first fixed pulley 410.

To this end, a first fixing member 222 is coupled to one side of the lower portion of the main frame 220 and protrudes rearward, and a fixing member bracket 315 is coupled to the pair of movable frames 312 in a crossing manner. Also, a second fixing member 316 is coupled to the center of the fixing member bracket 315 and protrudes rearward.

In this case, one end of the first wire 430 is coupled to the first fixing member 222, and the opposite end thereof is coupled to the second fixing member 316 via the pair of movable pulleys 420 and the first fixed pulley 410. Thus, the main column 200 and the sub-column 300 are connected by the first wire 430.

An elastic member 470 is arranged on one side of the first fixed pulley 410. While this embodiment illustrates a tension spring as the elastic member 470, this is merely one example. Various types of the elastic member 470 that provide elastic force, such as a gas springs or torsion spring, may be applied as needed.

The elastic member 470 is connected to a pair of cam pulleys 460 by a pair of third wires 490. For example, a third fixing member 471 may be provided at the upper end of the elastic member 470, and one end of each of the third wires 490 may be coupled to the corresponding one of both ends of the third fixing member 471. The opposite end of the pair of third wire 490 is coupled to the third wire fixing part 462 via the second winding groove 461 of the cam pulley 460. Accordingly, when the cam pulley 460 rotates, the third wires 490 are wound around the cam pulley 460.

According to the first embodiment of the present disclosure, an interlocking mechanism that allows the first sub-column 310 and the second sub-column 320 to be lifted and lowered in connection with each other may be provided, which will be described with reference to FIGS. 7 and 9.

Figure 7:
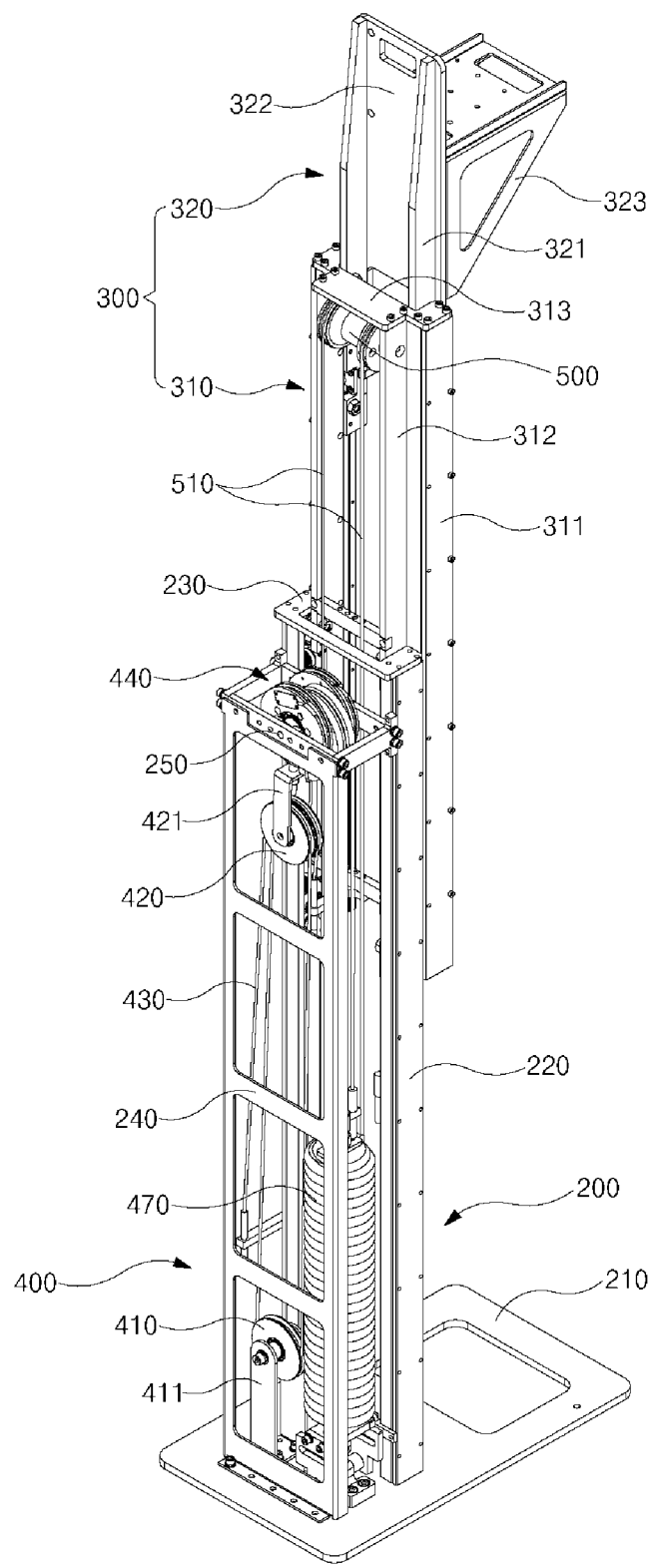
Figure 8:
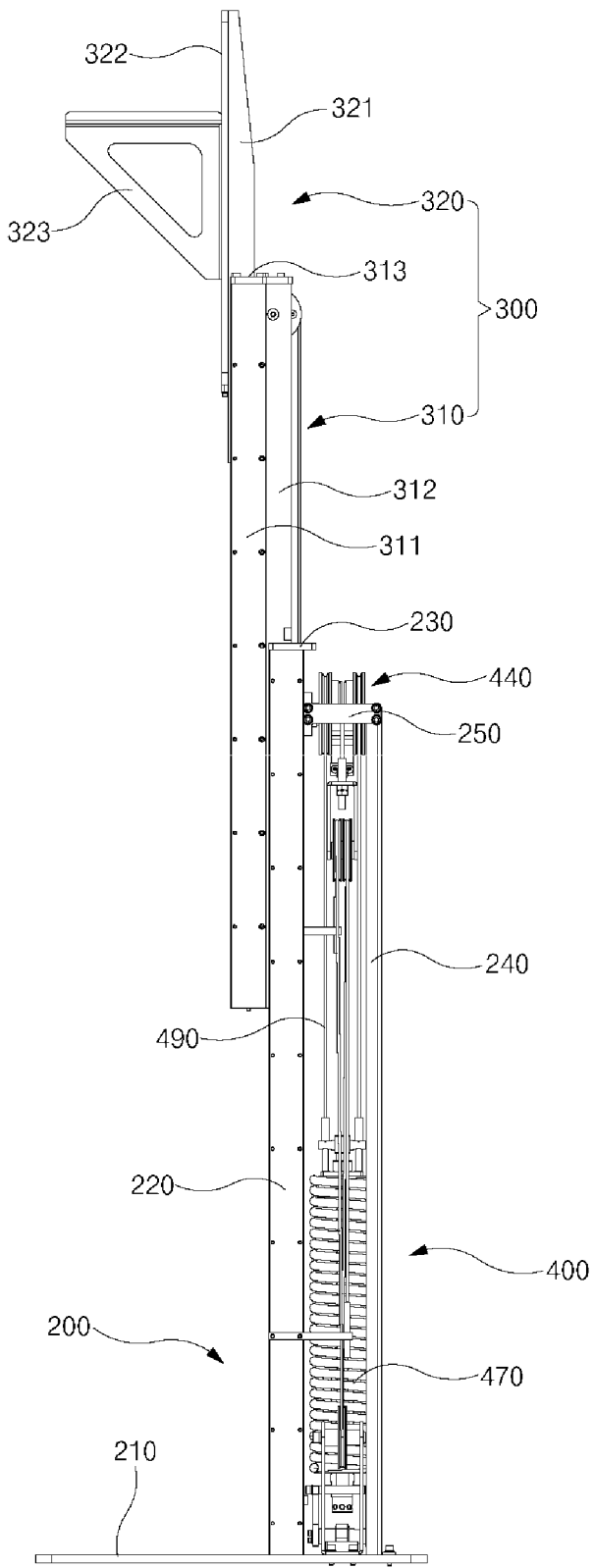
FIG. 8 is a side view of the telescopic column according to the first embodiment of the present disclosure.
Figure 9:
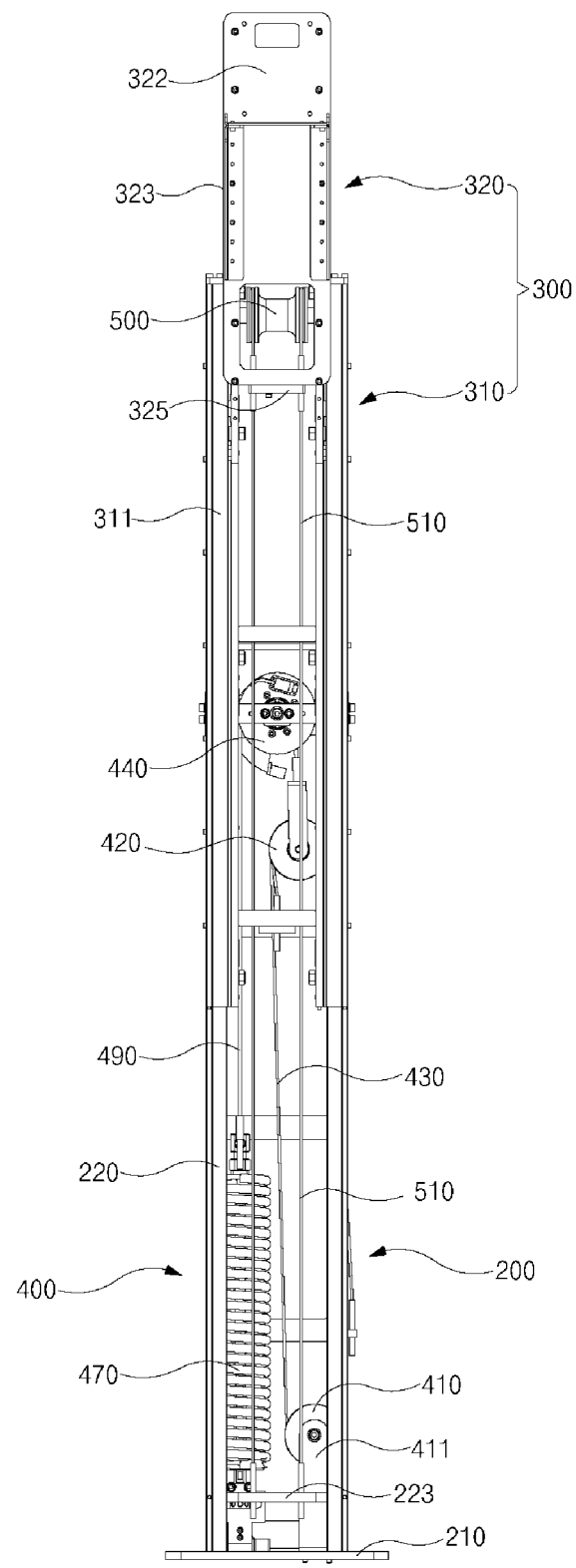
FIG. 9 is a front view of the telescopic column according to the first embodiment of the present disclosure.
Figure 10:
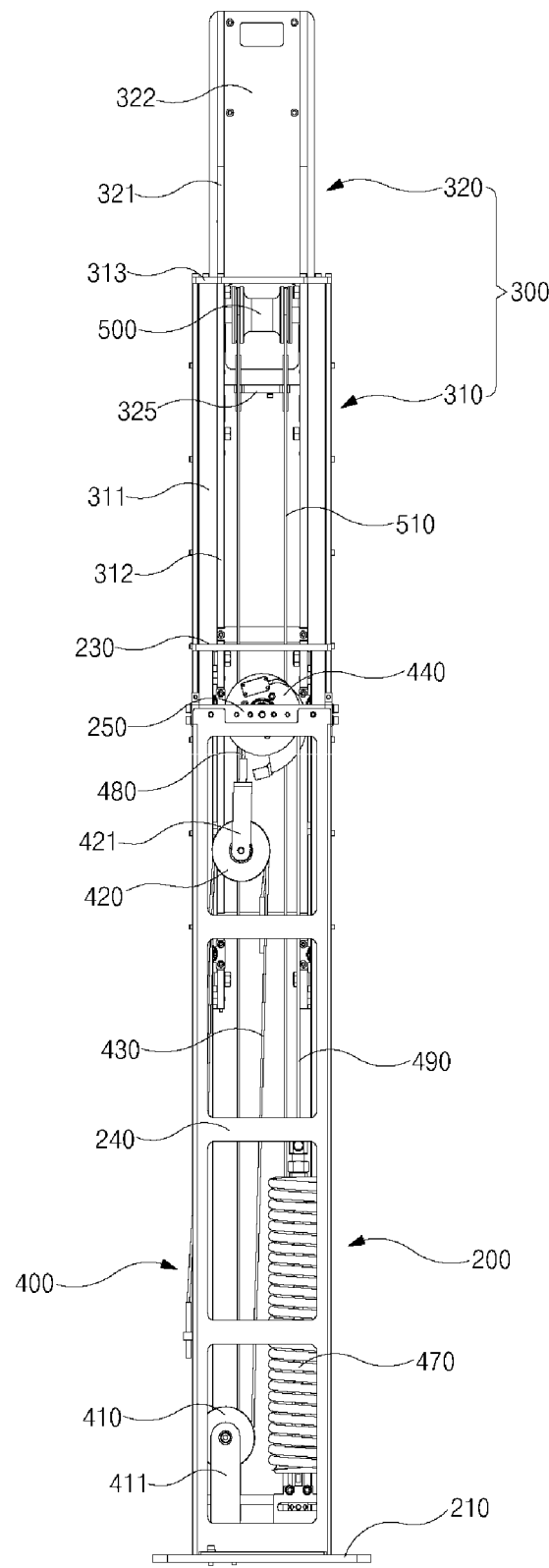
FIG. 10 is a rear view of the telescopic column according to the first embodiment of the present disclosure.

Referring to FIGS. 7 and 9, a second fixed pulley 500 is rotatably arranged at the upper end of the first sub-column 310. The second fixed pulley 500 is rotatably supported by a rotation shaft arranged across the upper ends of the movable frames 312, and a fourth wire 510 extends around the second fixed pulley 500 to connect the main column 200 and the second sub-column 320.

In this case, a fourth fixing member 223 is coupled to the lower portion of the main column 200 across the main frames 220, and one end of the fourth wire 510 is coupled to the fourth fixing member 223. The opposite end of the fourth wire 510 is coupled to a fifth fixing member 325 coupled to the lower end of the lifting plate 322 of the second sub-column 320.

In this case, a pair of winding grooves spaced apart from each other by a predetermined distance may be formed in the second fixed pulley 500, and a pair of fourth wires 510 may be arranged one in each winding groove, and be coupled to the fourth fixing member 223 of the main column 200 and the fifth fixing member 325 of the second sub-column 320 via the second fixed pulley 500, respectively.

Hereinafter, the lifting operation of the telescopic column 100 for an X-ray imaging apparatus according to the first embodiment of the present disclosure will be described in detail.

When the user presses down on the second sub-column 320 to lower the same at the maximum height at which the first sub-column 310 and the second sub-column 320 are positioned lifted with respect to the main column 200, The fourth wire 510 coupled to the lifting plate 322 of the second sub-column 320 at one end thereof presses the second fixed pulley 500 to lower the first sub-column 310. When the first sub-column 310 is lowered, the movable pulley 420 is lowered toward the first fixed pulley 410 by the first wire 430, and the second wire 480 wound around the cam 450 is unwound to rotate the cam 450. Then, the cam pulley 460, which rotates together with the cam 450, winds the third wire 490 to extend the elastic member 470.

Conversely, when the user lifts the second sub-column 320 upward from the minimum height at which the first sub-column 310 and the second sub-column 320 are positioned lowered with respect to the main column 200, the first sub-column 310 rises together with the sub-column 320. Then, the third wire 490 wound around the cam pulley 460 is unwound due to the elastic recovery force of the elastic member 470, and the cam pulley 460 rotates. Then, the cam 450 rotates together with the cam pulley 460 and winds the second wire 480 to lift the movable pulley 420, causing the first sub-column 310 to rise.

In this operation, the elastic force of the elastic member 470 compensates for the weight of the first and second sub-columns 310 and 320, allowing the user to easily lift the first and second sub-columns 310 and 320 with little effort. In addition, when the elastic force of the elastic member 470 changes, the torque of the cam 450 acts as a reaction torque with respect to the torque of the cam pulley 460, thereby compensating for the difference between the elastic force of the elastic member 470 and the weight of the first and second sub-columns 310 and 320, as described above.

In the case of the above-described embodiment, an interlocking-type telescopic column in which the second sub-column 320 is lifted and lowered in connection with the lifting and lowering of the first sub-column 310 has been described as an example. However, the weight compensator 400 including the cam 450 and the elastic member 470 according to the first embodiment of the present disclosure is also applicable to a non-interlocking-type telescopic column configured to lift the first sub-column 310 after the lifting of the second sub-column 320 is completed, or to lift the second sub-column 320 after the lifting of the first sub-column 310 is completed.

FIGS. 15 to 26 are views of a telescopic column for an X-ray apparatus according to a second embodiment of the present disclosure. A telescopic column 1000 for an X-ray imaging apparatus includes a main column 2000, a sub-column 3000 liftably mounted on the main column 2000, and a weight compensator 4000 configured to compensate for the weight of the sub-column 3000.

The weight compensator 4000 includes a first fixed pulley 4100 and a movable pulley 42000, which are mounted on the main column 2000, and a first wire 4300 connecting the main column 2000 and the sub-column 3000, a cam 4410 that varies the winding radius of a wire based on the lifting height of the sub-column 3000, and an elastic member 4500 arranged to extend and contract with the rotation of the cam 450 to provide elastic force.

The main column 2000 may be installed vertically on the body 1 (see FIG. 1) of the mobile X-ray imaging apparatus, and a hollow part is formed therein to allow the weight compensator 4000 including multiple pulleys and wires to be installed.

The sub-column 3000 is liftably disposed on one side of the main column 2000. In one example, a slide rail (not shown) may be formed on one side of the main column 2000, and the sub-column 3000 may be provided with multiple rollers slidably movable along the slide rail of the main column 2000 in a vertical direction.

An arm 3 (see FIG. 1) having an X-ray source 4 (see FIG. 1) at an end thereof may be liftably mounted on one side of the sub-column 3000. In this case, the arm may be multistage telescopically formed, and the weight compensator 400 compensates for the weight of the sub-column 3000 including the X-ray source and the arm.

The weight compensator 4000 may include the first fixed pulley 4100 rotatably disposed at an upper end of the main column 2000, the movable pulley 4200 liftably disposed below and spaced apart from the first fixed pulley 4100, and a first wire 4300 extending through the first fixed pulley 4100 and the movable pulley 4200 to connect the main column 2000 and the sub-column 3000.

Here, the number of first fixed pulleys 4100 and movable pulleys 4200 may be appropriately selected as needed. In one example, the first wire 4300 may be coupled to the upper end of the main column 2000 at one end, wound around the circumference of the movable pulleys 4200 and the first fixed pulley 4100 multiple times, and coupled to the sub-column 3000 at an opposite end.

As the first wire 4300 connects the main column 2000 and the sub-column 3000 via the first fixed pulley 4100 and the movable pulley 4200, the movable pulley 4200 is lifted and lowered with respect to the first fixed pulley 4100 when the sub-column 3000 is lifted and lowered with respect to the main column 2000.

In this case, the lifting and lowering of the sub-column 3000 may be performed manually by the user, and the weight compensator 4000 serves to make it possible to easily raise the sub-column 3000 with little effort, despite the weight of the sub-column 3000.

To this end, the elastic member 4500, which provides elastic force to the sub-column 3000, is disposed in the hollow part of the main column 2000. The elastic member 4500 is arranged to extend and retract according to the lifting and lowering of the movable pulley 4200, and provides an elastic force to the sub-column 3000 in connection with the movable pulley 4200 to compensate for the weight of the sub-column 3000. For example, when the elastic force provided by the elastic member 4500 is in balance with the weight of the sub-column 3000, the user may easily lift and lower the sub-column 3000 with little effort.

The elastic force provided by the elastic member 4500 may change as the sub-column 3000 is lifted and lowered. For example, when a tension spring is employed as the elastic member 4500, the tension spring may be increasingly stretched as the sub-column 3000 is lowered, thereby increasing the elastic force and thereby increasing the force required for the user to lower the sub-column.

The cam unit 4400 is provided to enable the sub-column 3000 to be lifted and lowered with uniform force regardless of changes in the lifting height of the sub-column 3000. The cam unit 4400 may be arranged to rotate in connection with the lifting and lowering of the traveling pulley 4200. For example, one end of the second wire 4600 may be coupled to one side of the movable pulley 4200 and the opposite end thereof may be wound on one side of the cam unit 4400. If necessary, the second wire 4600 may extend around the third fixing pulley 4700 arranged on one side of the elastic member 4500 and be wound on the one side of the cam unit 4400.

Additionally, the elastic member 4500 may be arranged to extend and contract in connection with the rotation of the cam unit 4400. For example, one end of the third wire 4800 may be coupled to the elastic member 4500 and the opposite end thereof may be coupled to the opposite side of the cam unit 4400.

More specifically, the cam unit 4400 may include a cam 4410 formed such that a winding radius of the second wire 4600 changes when rotated, and a cam pulley 4430 arranged on one side of the cam 4410 to rotate integrally with the cam 4410, the third wire 4800 being wound around the cam pulley 4430.

In this case, when the sub-column 3000 rises, the tension spring contracts and the cam pulley 4430 rotates such that the third wire 4800 is released. Then, as the cam 4410 rotates together with the cam pulley 4430, the second wire 4600 is wound around the cam 4410, and the second wire 4600 pulls the movable pulley 4200 downward.

Conversely, when the sub-column 3000 is lowered, the movable pulley 4200 rises, and the cam 4410 rotates such that the second wire 4600 is unwound. Then, as the cam pulley 4430 rotates together with the cam 4410, the third wire 4800 is wound around the cam pulley 4430, and the tension spring is extended by the third wire 4800.

Here, the cam 4410 has a cam profile that is formed such that the winding radius of the second wire 4600 changes when the cam is rotated (see FIG. 4). This is intended to cause the torque of the cam pulley 4430 due to the extension and contraction of the elastic member 4500 and the torque of the cam 4410 due to the lifting and lowering of the movable pulley 4200 to act as a reaction torque against each other, such that the sub-column 3000 can be lifted and lowered with uniform force regardless of its height. For example, the spring force of the tension spring and the torque of the cam pulley 4430 may be calculated according to the rotation angle of the cam pulley 4430, and the radius of the cam 4410 for compensating for the torque is calculated from the torque of the cam 4410 to derive a cam profile according to the rotation angle of the pulley 4430.

The cam 4410 has a radius gradually increasing in one direction along the circumference, and has an outer circumferential surface formed in a spiral shape within a predetermined angle range corresponding to the lifting range of the sub-column 3000, and a straight surface formed at an end of the spiral outer circumferential surface. In addition, a winding groove 4420 (see FIG. 25) for winding the second wire 4600 is formed on the spiral outer circumferential surface of the cam 4410, and a fixing part for fixing the second wire 4600 is formed on one side of the straight surface.

Accordingly, when the tension spring is extended and the torque of the cam pulley 4430 increases as the sub-column 3000 is lowered, the winding radius of the second wire 4600 of the cam 4410 gradually increases to increase the torque of the cam 4410. In this operation, the torque of the cam 4410 acts as a reaction torque with respect to the torque of the cam pulley 4430 to compensate for the difference between the elastic force of the tension spring and the weight of the sub-column 3000, and the user may be allowed to lift the sub-column 3000 with uniform force regardless of the height of the sub-column 3000 or the extension length of the tension spring.

Referring to FIGS. 17 to 21, it can be seen in more detail that the telescopic column 1000 for an X-ray apparatus includes the main column 2000, the sub-column 3000 liftably mounted on one side of the main column 2000, and the weight compensator 4000 mounted on the main column 2000 to compensate for the weight of the sub-column 3000.

A support plate 2100 may be coupled to the lower end of the main column 2000 to support the main column 2000. This support plate 2100 may be coupled to the body of the mobile X-ray imaging apparatus.

The main column 2000 includes a pair of main frames 2200 arranged vertically and spaced apart from each other by a predetermined distance in the width direction of the support plate 2100, and an upper end frame 2300 coupled to an upper end of the pair of main frames 2200, and a pair of support frames 2400 arranged in parallel with the main frames 2200 at a predetermined distance from the rear of the main frames 2200.

The main frames 2200 serve to guide the lifting direction of the sub-column 3000. The multiple pulleys constituting the weight compensator 4000 are arranged in the support frames 2400.

The sub-column 3000 may include a first sub-column 3100 liftably mounted on one side of the main column 2000, and a second sub-column 3200 liftably mounted on one side of the first sub-column 3100.

The first sub-column 3100 is liftably mounted to the front of the main column 2000, and includes a pair of sub-frames 3110 vertically slidably coupled to the front of the pair of main frames 2200, and a pair of movable frames 3120 mounted alongside the sub-frames 3110 on the inner side of the rear of the pair of sub-frames 3110. The pair of sub-frames 3110 and the pair of movable frames 3120 are integrally coupled by a cover frame 3130 coupled at the top thereof and a lower end frame 3140 coupled to the bottom thereof.

The second sub-column 3200 is liftably mounted to the front of the first sub-column 3100. The second sub-column 3200 includes a pair of lifting frames 3210 each vertically slidably coupled to an inner side of the pair of sub-frames 3110, a lifting plate 3220 coupled to a front of the pair of lifting frames 3210 and disposed in front of the sub-frames 3110, and an arm support bracket 3230 coupled to a front of the lifting plate 3220. Although not shown in the figures, the arm support bracket 3230 may be coupled to the arm that is multi-stage telescopic and includes the X-ray source at an end thereof.

Hereinafter, the lifting structure of the first sub-column 3100 and the second sub-column 3200 with respect to the main column 2000 will be described in detail with reference to FIGS. 22 and 23.

Figure 22:
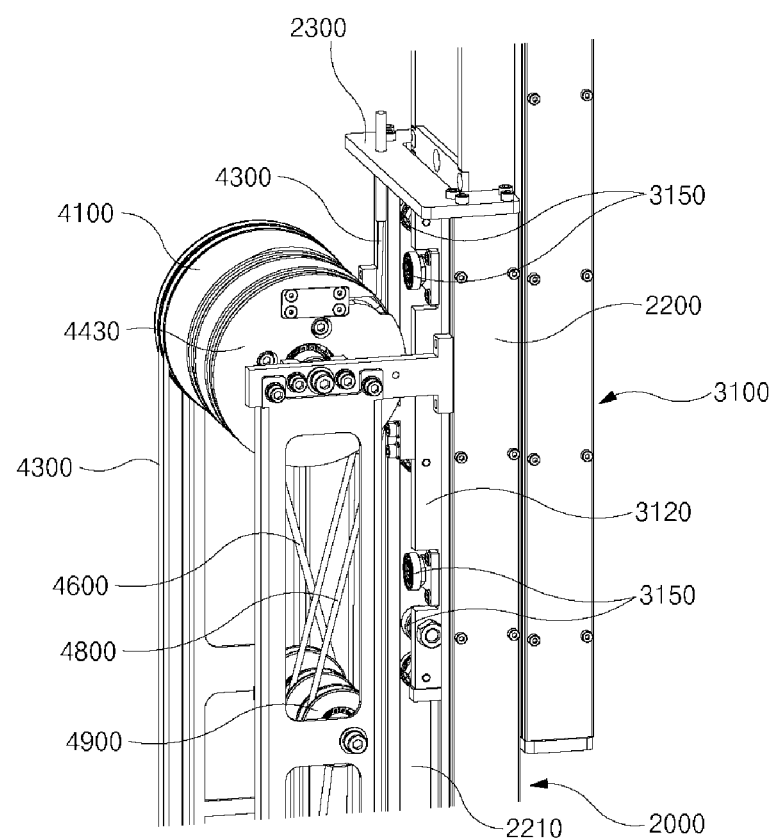
FIG. 22 is a partially enlarged view illustrating the slide engagement of a main column and a first sub-column according to the second embodiment of the present disclosure.

As shown in FIG. 22, the first sub-column 3100 is provided with multiple first rollers 3150 on the outside of the pair of movable frames 3120. The first rollers 3150 are slidably coupled to a first slide groove 2210 formed inside the main frames 2200 of the main column 2000. Accordingly, when the first sub-column 3100 is lifted or lowered with respect to the main column 2000, the first rollers 3150 of the movable frames 3120 move along the first slide groove 2210 of the main frames 2200.

Figure 23:
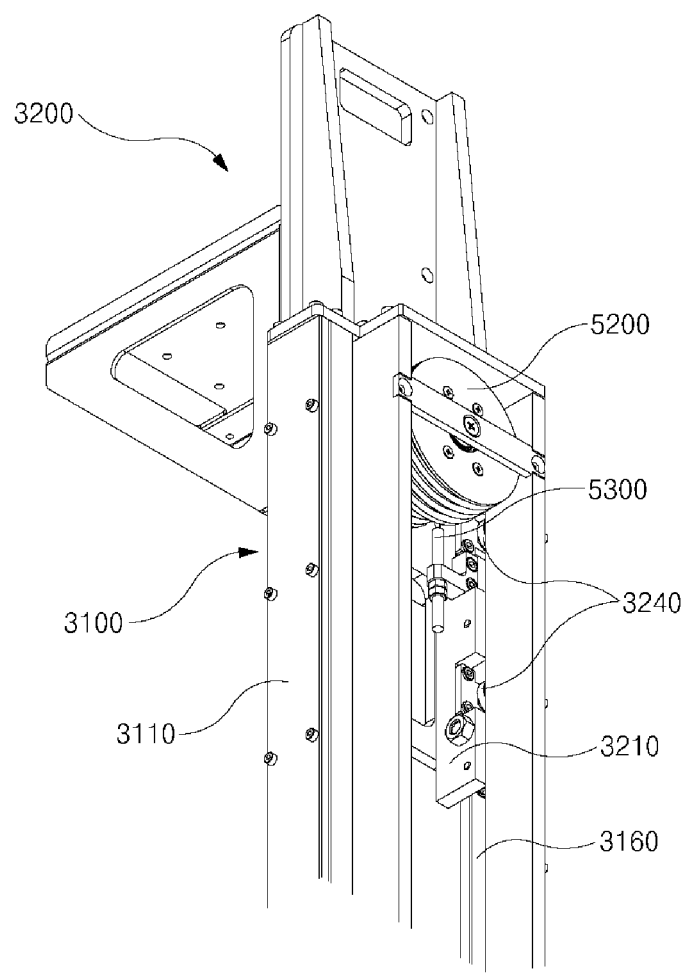
FIG. 23 is a partially enlarged view illustrating the slide engagement of the first sub-column and a second sub-column according to the second embodiment of the present disclosure.

As shown in FIG. 23, the second sub-column 3200 is provided with multiple second rollers 3240 on the outside of the pair of lifting frames 3210. The second rollers 3240 are slidably coupled to a second slide groove 3160 formed inside the sub-frame 3110 of the sub-column 3100. Accordingly, when the second sub-column 3200 is lifted and lowered with respect to the first sub-column 3100, the second rollers 3240 of the lifting frame 3210 move along the second slide groove 3160 of the sub-frame 3110.

Figure 24:
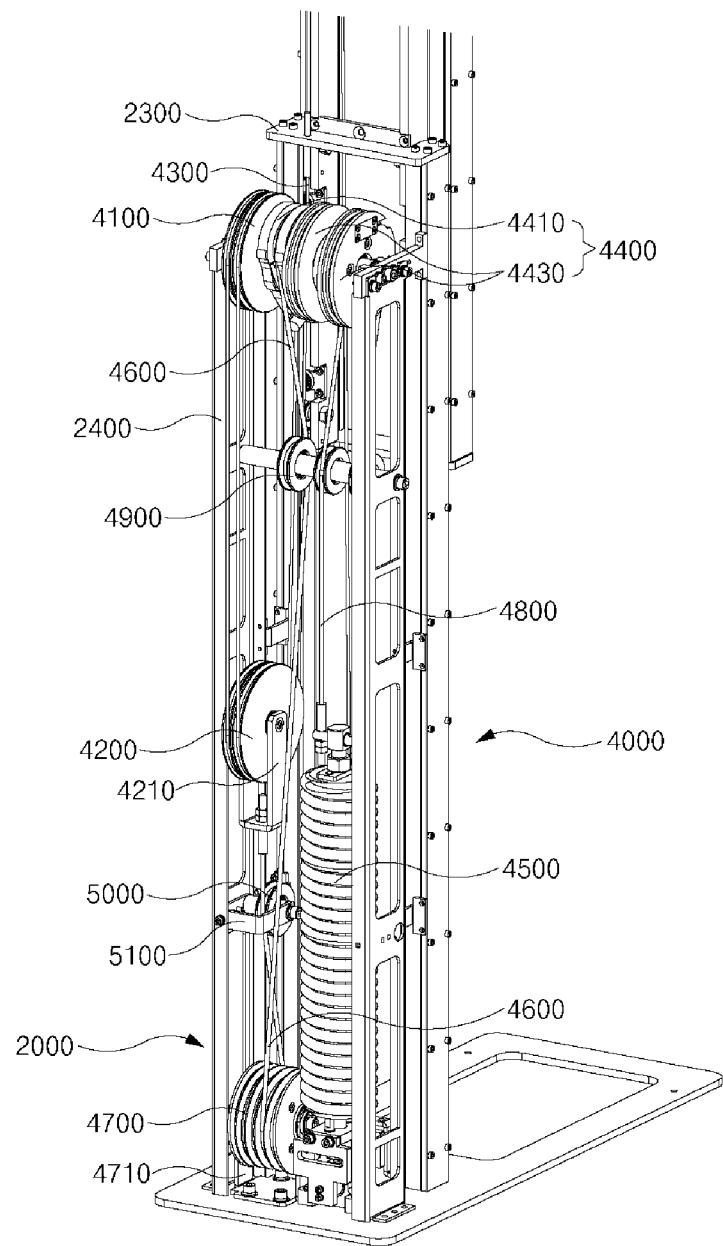
FIG. 24 is a partially enlarged view of the main column showing a weight compensator according to the second embodiment of the present disclosure.

As shown in FIG. 24, a first fixed pulley 4100 and a cam unit 4400 are rotatably arranged at the upper end of the support frame 2400 of the main column 2000. In this case, the first fixed pulley 4100 and the cam unit 4400 are coaxially coupled, while the first fixed pulley 4100 and the cam unit 4400 rotate independently of each other. That is, the cam unit 4400 is rotatably coupled to the rotation shaft of the first fixed pulley 4100 by, for example, a bearing (not shown).

Figure 25:
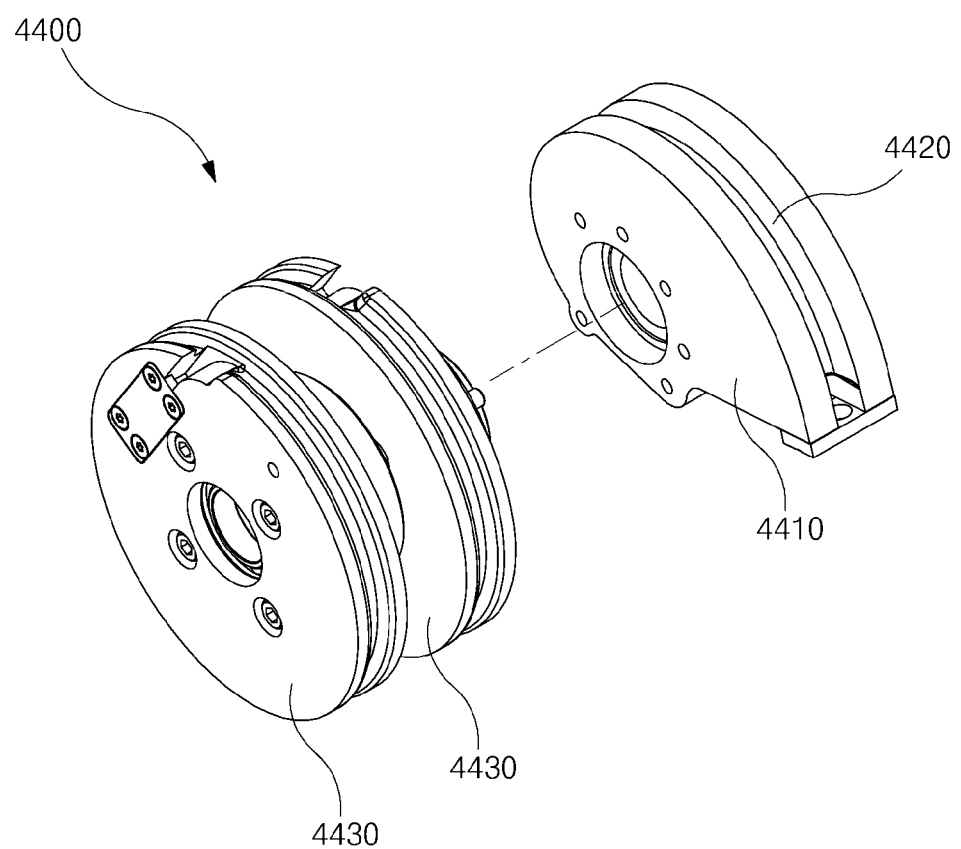
FIG. 25 is a perspective view of a cam unit according to the second embodiment of the present disclosure.

As shown in FIG. 25, the cam unit 4400 includes a cam 4410 whose winding radius changes, and at least one cam pulley 4430 arranged on one side of the cam 4410 to integrally rotate with the cam 4410. The cam 4410 and the cam pulleys 4430 may be formed as one body. In another example, the cam 4410 and the cam pulley 4430 may be formed as separate members and then rotatably coupled to each other to form one body.

Referring back to FIG. 24, a plurality of first guide pulleys 4900 is arranged below the first fixed pulley 4100 and the cam unit 4400 to be rotatable by a rotation shaft. The first guide pulley 4900 serves to guide the winding direction of the wire wound around the cam 4410 and the wire wound around the cam pulley 4430.

The movable pulley 4200 is liftably arranged below the first guide pulley 4900, and a U shaped wire fixing bracket 4210 is coupled to the rotation shaft of the movable pulley 4200.

A third fixed pulley 4700 is arranged below the movable pulley 4200. For example, the third fixing pulley 4700 may be rotatably supported by a first support bracket 4710 coupled to the top surface of the support frame 2400.

A second guide pulley 5000 may be rotatably arranged between the movable pulley 4200 and the third fixed pulley 4700 by a second support bracket 5100. The second guide pulley 5000 has one end coupled to the wire fixing bracket 4210 and serves to guide the movement direction of the second wire 4600 extending upward via the third fixing pulley 4700.

Figure 26:
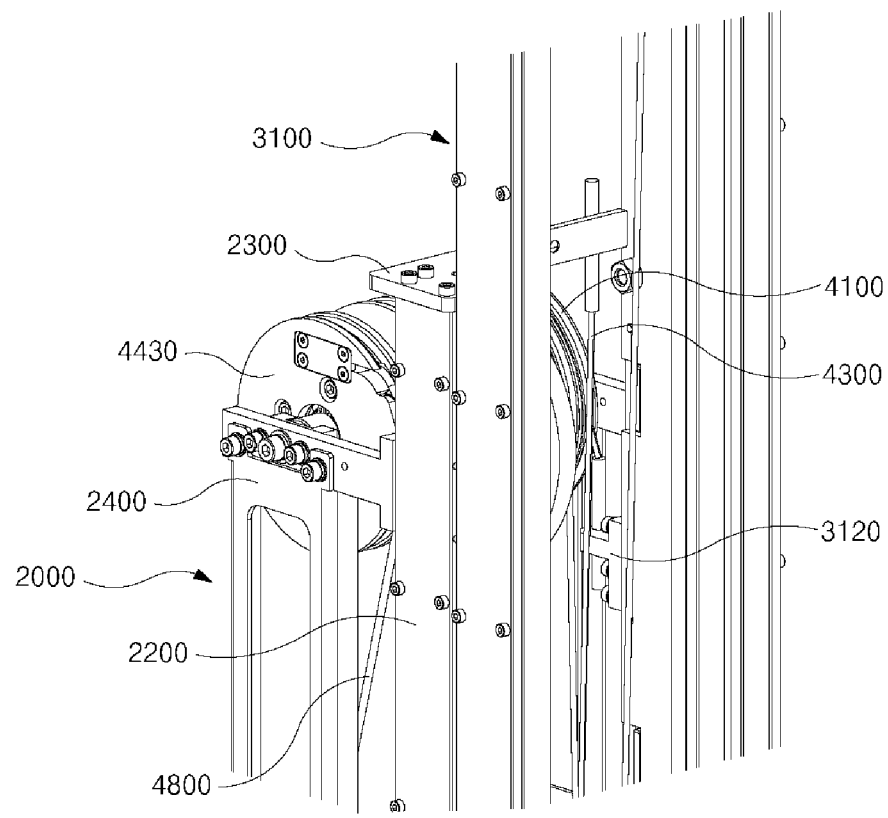
FIG. 26 is a partial enlarged view of a first wire connecting the main column and the first sub-column according to the second embodiment of the present disclosure.

A first wire 4300 connects the main column 2000 and the first sub-column 3100 by extending around the first fixed pulley 4100 and the movable pulley 4200. Referring to FIGS. 24 and 26, one end of the first wire 4300 is coupled to the upper end frame 2300 of the main column 2000 by a fixing member, and the opposite end thereof is coupled to the moving frame 3120 of the first sub-column 3100 by the fixing member after being wound around the movable pulley 4200 and the first fixed pulley 4100 multiple times. Accordingly, when the first sub-column 3100 is lifted or lowered, the movable pulley 4200 is lifted or lowered with respect to the first fixed pulley 4100.

Referring again to FIG. 24, a second wire 4600 is connected between the movable pulley 4200 and the cam unit 4400 such that the cam unit 4400 rotates in connection with the lifting and lowering of the movable pulley 4200. Specifically, one end of the second wire 4600 is coupled to the wire fixing bracket 4210, and the opposite end thereof is coupled to one side of the winding groove 4420 of the cam 4410 via the third fixing pulley 4700, Accordingly, when the movable pulley 4200 is lifted or lowered, the second wire 4600 is wound around or unwound from the cam 4410.

In addition, the cam pulley 4430 and the elastic member 4500 are connected by a third wire 4800. One end of the third wire 4800 is coupled to the upper end of the elastic member 4500, and the opposite end thereof extends upward and is wound around the cam pulley 4430. Accordingly, when the cam pulley 4430 rotates integrally with the cam 4410 as the cam 4410 rotates, the elastic member 4500 may extend and contract in connection therewith, and the cam 4410 may rotate together with the pulley 4430 in connection with the extension and contraction of the elastic member 4500.

According to the second embodiment of the present disclosure, an interlocking mechanism that allows the second sub-column 3200 to be lifted and lowered in connection with the lifting and lowering of the first sub-column 3100, which will be described with reference to FIGS. 20 and 21.

Figure 20:
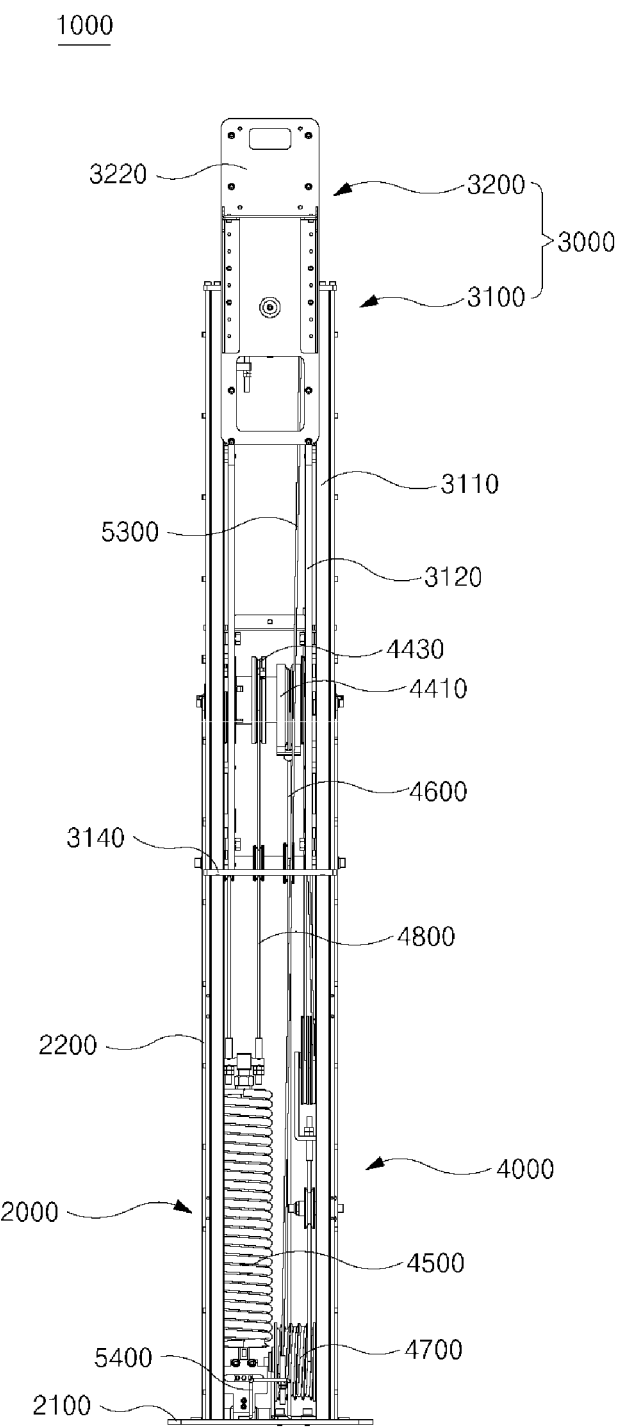
FIG. 20 is a front view of the telescopic column according to the second embodiment of the present disclosure.
Figure 21:
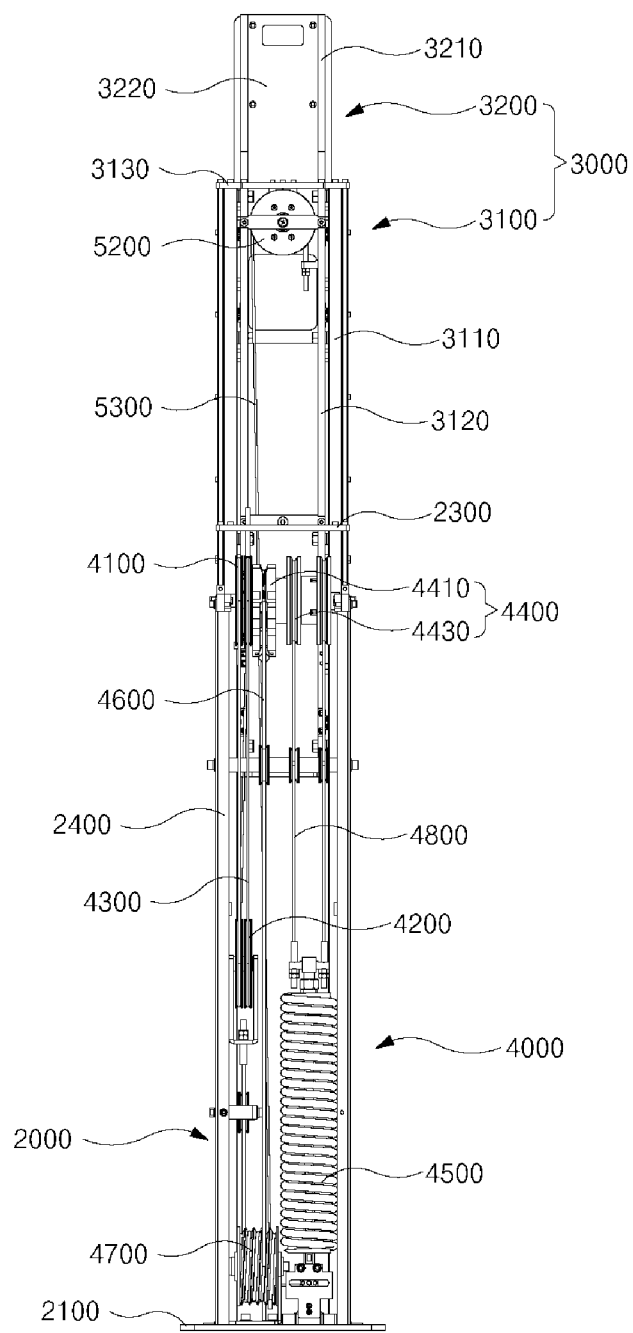
FIG. 21 is a rear view of the telescopic column according to the second embodiment of the present disclosure.

Referring to FIGS. 20 and 21, a fourth fixing pulley 5200 is rotatably arranged at the upper end of the first sub-column 3100, and a fourth wire 5300 extends around the fourth fixed pulley 5200 of the first sub-column 3100 and connects the main column 2000 and the second sub-column 3200.

Here, when the second sub-column 3200 is lifted and lowered in connection with the lifting and lowering of the first sub-column 3100, the fourth fixing pulley 5200 serves to determine the stroke ratio of the column 3200 to the second sub-column 3100. To this end, for example, the fourth fixed pulley 5200 may be composed of a two-stage radius pulley having two different radii.

In this case, one end of the fourth wire 5300 is coupled to the fixing bracket 5400 arranged on the top surface of the support plate 2100 at the lower portion of the main column 2000, and the opposite end thereof is coupled to the lifting frame 3210 of the second sub-column 3200 via the fourth fixed pulley 5200 (see FIG. 23).

Hereinafter, the lifting operation of the telescopic column 1000 for an X-ray imaging apparatus according to the second embodiment of the present disclosure will be described in detail.

When the user presses down on the second sub-column 3200 to lower the same at the maximum height at which the first sub-column 3100 and the second sub-column 3200 are positioned lifted with respect to the main column 2000, The fourth wire 5300 coupled to the lifting plate 322 of the second sub-column 32000 at one end thereof presses the fourth fixed pulley 5200 to lower the first sub-column 3100.

When the first sub-column 3100 is lowered, the movable pulley 4200 is lifted toward the first fixed pulley 4100 by the first wire 4300, the second wire 4600 wound around the cam 4410 is released, and the cam 4410 rotates. Also, the cam pulley 4430, which rotates together with the cam 4410, winds the third wire 4800 to extend the elastic member 4500.

Conversely, when the user lifts the second sub-column 3200 upward from the minimum height at which the first sub-column 3100 and the second sub-column 3200 are positioned lowered with respect to the main column 2000, the second sub-column 3200 rises together with the first sub-column 3100. Then, the third wire 4800 wound around the cam pulley 4430 is unwound by the elastic force of the elastic member, causing the cam pulley 4430 to rotate. Then, the cam 4410 rotates together with the cam pulley 4430 and winds the second wire 4600 to lower the movable pulley 4200.

In this case, the stroke ratio of the second sub-column 3200, which is lifted and lowered in connection with the lifting and lowering of the first sub-column 3100, is determined by the fourth fixed pulley 5200 composed of a two-stage radius pulley. The elastic force of the elastic member 4500 serves to compensate for the weight of the first and second sub-columns 3100 and 3200 to allow the user to easily lower the first and second sub-columns 310 and 3200 with little effort.

In addition, when the elastic force of the elastic member 4500 changes, the torque of the cam 4410 acts as a reaction torque with respect to the torque of the cam pulley 4430, thereby compensating for the difference between the elastic force of the elastic member 4500 and the weight of the first and second sub-columns 310 and 3200, as described above.

While the embodiments of the present disclosure have been described above, it will be appreciated by those skilled in the art that various modifications and changes can be made to the present disclosure without departing from the spirit and scope of the claims of the present disclosure.

According to the telescopic column for X-ray imaging apparatus of the present disclosure, the length of the column may be quickly and easily extended or shortened manually without a separate driving source or weight.

What is claimed is:

1. A telescopic column for an X-ray imaging apparatus, the telescopic column comprising:
   a main column;
   a sub-column liftably arranged on one side of the main column; and
   a weight compensator arranged on an opposite side of the main column to compensate for a weight of the sub-column,
   wherein the weight compensator comprises:
   a cam formed such that a radius of winding of a wire therearound changes when the cam is rotated according to a lifting height of the sub-column; and
   an elastic member configured to extend and contract according to rotation of the cam to provide elastic force to compensate for the weight of the sub-column,
   wherein a radius of the cam gradually increases in one direction along a circumference of the cam at a predetermined angle range, and the cam has a curved surface formed in a spiral shape within the predetermined angle range.

2. The telescopic column of claim 1, wherein the weight compensator comprises:
   a first fixed pulley arranged on the main column;
   a movable pulley arranged to be lifted and lowered with respect to the first fixed pulley;
   a first wire having one end coupled to the main column and an opposite end coupled to the sub-column via the movable pulley and the first fixed pulley;
   a cam unit arranged to rotate in connection with the lifting and lowering of the movable pulley; and
   the elastic member arranged to extend and contract in connection with the rotation of the cam unit to provide elastic force to the sub-column.

3. The telescopic column of claim 1, wherein the sub-column comprises:
   a first sub-column liftably arranged on one side of the main column; and
   a second sub-column liftably arranged on one side of the first sub-column.

4. The telescopic column of claim 3, further comprises:
an interlocking mechanism configured to lift and lower the second sub-column in connection with lifting and lowering of the first sub-column,
wherein the interlocking mechanism comprises:
a second fixing pulley arranged at an upper end of the first sub-column; and
a fourth wire having one end coupled to the main column and an opposite end coupled to the second sub-column via the second fixing pulley.

5. A telescopic column for an X-ray imaging apparatus, the telescopic column comprising:
a main column;
a sub-column liftably arranged on one side of the main column; and
a weight compensator arranged on an opposite side of the main column to compensate for a weight of the sub-column,
wherein the weight compensator comprises:
a first fixed pulley arranged on the main column;
a movable pulley arranged to be lifted and lowered with respect to the first fixed pulley;
a first wire having one end coupled to the main column and an opposite end coupled to the sub-column via the movable pulley and the first fixed pulley;
a cam unit arranged to rotate in connection with the lifting and lowering of the movable pulley;
an elastic member arranged to extend and contract in connection with rotation of the cam unit to provide elastic force to the sub-column;
a second wire having one end coupled to one side of the movable pulley and an opposite end wound on one side of the cam unit; and
a third wire having one end coupled to the elastic member and an opposite end wound on an opposite side of the cam unit.

6. The telescopic column of claim 5, wherein the cam unit comprises:
a cam formed such that a radius of winding of the second wire therearound changes when the cam rotates; and
a cam pulley arranged on one side of the cam to rotate integrally with the cam, the third wire being wound around the cam pulley.

7. The telescopic column of claim 6, wherein a torque of the cam caused by lifting and lowering of the movable pulley acts as a reaction torque against a torque of the cam pulley caused by extension and contraction of the elastic member.

8. The telescopic column of claim 5, wherein the weight compensator further comprises:
a third fixed pulley arranged on one side of the elastic member,
wherein the second wire is wound on one side of the cam unit via the third fixed pulley.

9. The telescopic column of claim 8, wherein the sub-column comprises:
a first sub-column liftably arranged on one side of the main column; and
a second sub-column liftably arranged on one side of the first sub-column,
the telescopic column further comprising:
an interlocking mechanism configured to lift and lower the second sub-column in connection with lifting and lowering of the first sub-column,
wherein the interlocking mechanism comprises:
a fourth fixing pulley arranged at an upper end of the first sub-column; and
a fourth wire having one end coupled to the one side of the main column and an opposite end coupled to one side of the second sub-column via the fourth fixing pulley.

10. A telescopic column for an X-ray imaging apparatus, the telescopic column comprising:
a main column;
a sub-column liftably arranged on one side of the main column; and
a weight compensator arranged on an opposite side of the main column to compensate for a weight of the sub-column,
wherein the sub-column comprises:
a first sub-column liftably arranged on one side of the main column; and
a second sub-column liftably arranged on one side of the first sub-column,
wherein the weight compensator comprises:
a first fixed pulley arranged on a lower portion of the main column;
a movable pulley arranged above the first fixed pulley to be lifted and lowered with respect to the first fixed pulley;
a first wire having one end coupled to the main column and an opposite end coupled to the sub-column via the movable pulley and the first fixed pulley;
a cam arranged to rotate in connection with the lifting and lowering of the movable pulley;
a pair of cam pulleys arranged on both sides of the cam to rotate integrally with the cam;
a second wire having one end coupled to one side of the movable pulley and an opposite end wound around the cam;
an elastic member arranged to extend and contract in connection with rotation of the cam pulley;
a third wire having one end wound around the cam pulley and an opposite end coupled to the elastic member;
a second fixed pulley rotatably arranged at an upper end of the first sub-column; and
a fourth wire having one end coupled to the second sub-column and an opposite end coupled to the main column via the second fixed pulley.

* * * * *